United States Patent [19]

Harpel

[11] Patent Number: 4,629,694
[45] Date of Patent: Dec. 16, 1986

[54] DETECTING AND DISTINGUISHING BETWEEN PLASMINOGEN ACTIVATORS

[75] Inventor: Peter C. Harpel, New York, N.Y.

[73] Assignee: Cornell Research Foundation, Inc., Ithaca, N.Y.

[21] Appl. No.: 513,184

[22] Filed: Jul. 12, 1983

[51] Int. Cl.[4] .................. G01N 33/53; C12Q 1/56; C12N 1/72; C12N 1/68
[52] U.S. Cl. ........................................ 435/7; 435/13; 435/215; 435/217
[58] Field of Search .................. 435/7, 174, 13, 214, 435/215, 216, 217

[56] References Cited

U.S. PATENT DOCUMENTS

| | | |
|---|---|---|
| 3,730,843 | 5/1973 | McKie . |
| 3,932,221 | 1/1976 | Pfleiderer et al. . |
| 4,046,634 | 9/1977 | Mercer . |
| 4,100,028 | 7/1978 | Stepanov et al. . |
| 4,134,792 | 1/1979 | Boguslaski et al. . |
| 4,198,335 | 4/1980 | Collen et al. . |
| 4,231,999 | 11/1980 | Carlsson et al. . |
| 4,233,401 | 11/1980 | Yoshida et al. . |
| 4,273,866 | 6/1981 | Voss et al. . |
| 4,332,783 | 6/1982 | Pernice et al. . |
| 4,342,566 | 8/1982 | Theofilopoulos et al. . |
| 4,353,982 | 10/1982 | Gomez et al. . |

FOREIGN PATENT DOCUMENTS

| | | |
|---|---|---|
| 2952478 | 7/1981 | Fed. Rep. of Germany . |
| 3016575 | 11/1981 | Fed. Rep. of Germany . |

OTHER PUBLICATIONS

Wiman et al. Nature 272:549-550 (1978).
Astrup, Fed. Proc. 25:42-51 (1966).
Moroz, New Engl. J. of Med. 296:525-529 (1977).
Lau et al., J. Biological. Chem., 254:8751-8761 (1979).
Monji et al., Res. Comm. Chem. Pathol. & Pharmacol, 26:187-196 (1979).
Camiolo et al., Proc. Soc. Exp. Biol. Med., 38:277-280 (1971).
Wallen, *Progress in Chemical Fibrinolysis and Thrombolysis,* Davidson, et al., eds., vol. 3, pp. 167-181 (1978).
Thorsen et al., Thrombos. Diathes. haemorrh., 28:65-74 (1972).
Hoylaerts et al., J. Biol. Chem., 257:2912-2919 (1982).
Matsuo et al., Thromb. Haemostas, 45:225-229 (1981).
Clemmensen et al., Biochem. Biophys. Acta., 429:591-599 (1976).
Clemmensen, Thrombos. Haemostas, 39:616-623 (1978).
Vahtera et al., Biochem. J., 171:767-770 (1978).
Murano et al., Blood, 55:430-436 (1980).
Korninget et al., Thromb. Haemostas, 46:662-665 (1981).
Harpel, et al., Analytical Biochem., 108:166-175 (1980).
Lewin et al., J. Biological Chem., 258:6415-6421 (1983).
Harpel et al., J. Clin. Invest., 68:46-55 (1981).
Brower et al., Blood, 61:842-849 (1983).
Jesty et al., Anal. Biochem., 139:158-167 (1984).
Inman et al., Clin. Exp. Immunol., 53:521-528 (1983).
Levin et al., J. Clin. Invest., 74:571-580 (1984).
Harpel et al., J. Clin. Invest., 52:2175-2184 (1973).
Plow et al., J. Lab. Clin. Med., 93:199-209 (1979).
Ohlsson et al., Clinica Chimica Acta, 66:1-7 (1976).

Primary Examiner—Christine M. Nucker
Assistant Examiner—Cynthia Lee Foulke
Attorney, Agent, or Firm—Jones, Tullar & Cooper

[57] ABSTRACT

This invention relates to a method for determining fibrinolytic activation in human blood and to a method to distinguish between tissue (e.g. vascular) plasminogen activator and urokinase-like plasminogen activator contributions to fibrinolytic activation.

Broadly, the method of the invention relates to detecting the level of plasmin-plasmin inhibitor complexes in blood plasma samples before and after clotting thereof; a greater increase in the complex level in the clotted sample as compared to non-clotted samples indicating the presence of circulating tissue plasminogen activator, with substantially identical levels of increase of complex in both the clotted and unclotted samples indicating the sole presence of urokinase-type plasminogen activator in the sample.

9 Claims, 12 Drawing Figures

DETECTING AND DISTINGUISHING BETWEEN PLASMINOGEN ACTIVATORS

The invention described herein was at least in part made in the course of work under a grant or award from the National Institutes of Health (Grant No. HL-18828).

BACKGROUND OF THE INVENTION

Plasminogen activation

Plasminogen is the precursor or inactive form of the proteolytic enzyme plasmin. Plasminogen is widely distributed in human tissues, fluids and the blood. Plasmin is the important enzyme that dissolves blood clots in the circulation. This enzyme also plays a role in tumor cell growth and spread, in implantation of the embryo and other physiological functions. Plasminogen is activated to plasmin by other proteolytic enzymes known as plasminogen activators. Two major groups of plasminogen activators have been described and partially characterized. The first is urokinase-type plasminogen activator. The prototype enzyme urokinase (UK) has been isolated from human urine or tissue culture of kidney cells. UK activates plasminogen to plasmin in purified systems and in blood, and is commercially available and used to achieve clot (thrombus) dissolution in patients. Many different tissues as well as tumors in tissue culture appear to synthesize UK or a UK-type activator.

The second type of plasminogen activator is non-urokinase enzyme. This tissue plasminogen activator is produced by some tumors in culture, notably a line of human melanoma cells, as well as by human uterine tissue. This type of activator appears also to be produced by the human blood vessel wall. This non-urokinase-plasminogen activator, to be called tissue-type or vascular plasminogen activator, activates plasminogen upon a fibrin surface, whereas the urokinase type activators do not require a fibrin clot network to activate plasminogen to plasmin. (The nomenclature "tissue type plasminogen activator" was adopted by the Subcommittee on Fibrinolysis of the International Committee on Thrombosis and Haemostasis in July 1982.)

Methods to measure plasminogen activator activity are available which are imprecise and semi-quantitative and which do not clearly distinguish between the two general types of plasminogen activators, both of which may occur in blood and in other body fluids. These methods generally include preparing a euglobulin fraction from plasma by diluting plasma at acid pH, and then testing the plasmin activity of this fraction on a fibrin or other suitable substrate. This methodology is susceptible to many variables, and provides inconsistent results.

Arterial thrombosis may be the major cause of acute myocardial infarction, Hammer, *Wien Med. Wochenschr.*, 28: 97-102 (1878) and De Wood et al, *N. Engl. J. Med.*, 303: 897-902 (1980) and stroke, Hunt, *Am. J. Med. Sci.*, 147: 704-713 (1914) and Genton et al, *Stroke*, 8: 159-175 (1977). The thrombotic process in these states can be initiated by platelet aggregation at sites of atherosclerotic obstruction, Folts et al, *Circulation*, 54: 365-370 (1976) and Gertz et al, *Circulation*, 63: 476-486 (1981) followed by coagulation and the formation of an occlusive fibrin clot; De Wood et al., *N. Engl. J. Med.*, 303: 897-902 (1980). Because aspirin prevents platelet aggregation by inhibiting cyclooxygenase and resultant production of thromboxane $A_2$, Vane, *Nature New Biol.*, 231: 232-235 (1971) and Smith et al, *Nature New Biol.*, 231: 235-237 (1971), it has been utilized in attempts to alter the natural history of atherosclerotic, Coronary Drug Project Research Group, *J. Chron. Dis.*, 29: 625-642 (1976), Elwood et al, *Lancet.*, i: 436-440 (1974), Elwood et al, *Lancet.*, i: 436-440 (1974), Elwood et al., *Lancet.*, ii: 1313-1315 (1979), Aspirin Myocardial Infarction Study Research Group, *JAMA.*, 243: 661-669 (1980) and Persantine-aspirin Reinfarction Study Research Group, *Circulation.*, 62: 449-461 (1980) and thromboembolic disease; Harris et al., *N. Engl. J. Med.*, 297: 1246-1249 (1977) and Canadian Cooperative Study Group, *N. Engl. J. Med.*, 299: 53-59 (1978). Few of these studies individually have successfully demonstrated a significant benefit from aspirin. The Canadian Cooperative Study showed that aspirin reduced the risk of stroke and death only in male patients; Canadian Cooperative Study Group, *N. Engl. J. Med.*, 299: 53-59 (1978). Similarly, Harris et al. showed that aspirin reduced the risk of postoperative thromboembolism, but once again only in men; Harris et al., *N. Engl. J. Med.*, 297: 1246-1249 (1977). None of the large trials of aspirin for the secondary prevention of myocardial infarction demonstrated statistically significant benefits from this drug, Coronary Drug Project Research Group, *J. Chron. Dis.*, 29: 625-642 (1976), Elwood et al., *Lancet.*, i: 436-440 (1974), Elwood et al., *Lancet.*, ii: 1313-1315 (1979), Aspirin Myocardial Infarction Study Research Group, *JAMA.* 243: 661-669 (1980) and Persantine-aspirin Reinfarction Study Research Group, *Circulation*, 62: 449-461 (1980), though beneficial trends were described.

While the effect of aspirin on platelets has been studied extensively, its effect on coagulation and fibrinolysis has been less well defined. Menon, *N. Engl. J. Med.*, 296: 525-529 (1977) and Moroz, *N. Eng. J. Med.*, 296: 525-529 (1977) both demonstrated an increase in whole blood fibrinolytic activity after ingestion of 1.8 g of aspirin, but Moroz showed that this was due entirely to the fibrinolytic action of cellular elements. In constrast, Ghezzo et al., *Acta. Haemat.*, 65: 229-232 (1981) showed a decrease in fibrinolysis induced by both cellular and plasma factors after ingestion of 1 g of aspirin per day for four days. Studies in animals have shown both an antithrombotic, Housholder, et al., *J. Oral Surg.*, 38: 412-416 (1980) and Zimmerman et al., *Artery.*, 8: 422-425 (1980) and a "paradoxical" thrombotic effect of aspirin; Zimmerman et al., *Artery.* 8: 422-425 (1980), Kelton et al., *J. Clin. Invest.*, 62: 892-895 (1978), Zimmerman et al., *Thromb. Res.*, 16: 843-846 (1979).

Fibrinolysis and the subsequent dissolution of blood clots depends on the formation of plasmin from the inactive precursor plasminogen by plasminogen activators; Astrup, *Fed. Proc.*, 25: 42-51 (1966), Wallen, *Progress in chemical fibrinolysis and thrombolysis.* New York, Raven Press, 3: 91-98 (1978) and Collen, *Thromb. Haemostas.*, 43: 77-89 (1980).

The method of the invention makes it possible, for example, to study the effect of aspirin or other drug which has multiple effects including an effect upon fibrinolysis induced by plasminogen activators and to select a dosage which, if possible, has desired effects while minimizing adverse fibrinolysis effects.

DESCRIPTION OF THE INVENTION

This invention relates to a method for determining fibrinolytic activation in human blood and to a method to distinguish between tissue (e.g. vascular) plasminogen activator and urokinase-like plasminogen activator contributions to fibrinolytic activation.

Broadly, the method of the invention relates to detecting the level of plasmin-plasmin inhibitor complexes in blood plasma samples before and after clotting thereof; a greater increase in the complex level in the clotted sample as compared to non-clotted sample indicating the presence of circulating tissue plasminogen activator, with substantially identical levels of increase of complex in both the clotted and unclotted samples indicating the sole presence of urokinase-like plasminogen activator in the sample.

In the method of this invention, plasminogen activator in mammalian blood is indirectly measured by a two-step time lapsed immunoassay which measures plasmin-naturally occurring plasmin inhibitor complexes.

In the method of the invention, the level of naturally occurring plasmin inhibitor (PI)-plasmin complexes and/or $\alpha$2-macroglobulin ($\alpha_2$M)-plasmin complexes in the blood plasma is first measured at time zero (within 30 minutes of extraction) in both a clotted and unclotted sample of the plasma. After a predetermined time, the level of naturally occurring plasmin inhibitor-plasmin complex is again measured. Where there is no significant difference between measured values after the predetermined time between the clotted and unclotted samples, any recent plasminogen activator activity was urokinase-type plasminogen activator activity. On the other hand where, over time, there is a significant increase in complex measured in the clotted sample as compared to the unclotted sample over that same time period, the blood sample contained significant tissue plasminogen type activator.

Where the curve is flat with time the indication is the complete absence or prior depletion of plasminogen activators in the blood as drawn.

If desired, as a control, several concentrations of tissue activator and/or urokinase can be added to samples to establish that the plasma sample being tested can respond to the pressure of such materials (i.e., the generation of standard curve for the particular plasma sample being tested).

It may in fact be desirable, to insure most accurate determination of plasminogen activator to add to the blood samples as drawn, either a predetermined amount of blood or a mixture of purified reagents such as plasmin inhibitor, plasminogen and fibrinogen to insure that sufficient of each reactant is present so that negative results are clearly attributable to the absence of plasminogen activator and not the absence of one of the other materials necessary to attain positive results.

It is pointed out that application Ser. No. 287,665, filed July 28, 1981, now abandoned, describes a method of measuring naturally occurring enzyme-inhibitor/enzyme complexes. That method is described as functioning to measure complexes present in the blood as drawn. In distinction, the present method depends on the generation of enzyme-enzyme inhibitor complexes in the blood samples after removal from the body.

The present method is based in part on the method described in application Ser. No. 287,665, that teaches a method for the detection and quantification of protease-naturally occurring protease inhibitor complexes. The principle of the present method is the demonstration that urokinase plasminogen activators convert plasminogen to plasmin in plasma in the absence of a fibrin clot.

The plasmin thus generated rapidly forms irreversible complexes with two plasma proteins known as $\alpha_2$-plasmin inhibitor (PI) and $\alpha$2-macroglobulin ($\alpha_2$M). In contrast, it was found that the non-UK, vascular plasminogen activator converts plasminogen to plasmin in unclotted plasma at a very low rate but converts plasminogen to plasmin in clotted plasma at a much higher rate with the generation of plasmin inhibitor-plasmin complexes. Thus, it is possible to document the activity of the various plasminogen activators by incubating plasma or clotted plasma to which either UK or melanoma activator has been added and following the production of naturally occurring plasmin inhibitor-plasmin complexes as outlined in application Ser. No. 287,665.

The methods employed for detecting and measuring the enzyme-naturally occurring enzyme inhibitor complexes is described in application Ser. No. 287,665, hereby incorporated by reference. One method broadly comprises forming an insoluble complex (E-I-anti I) comprising enzyme (E), enzyme inhibitor (I), and then detecting and identifying and preferably quantitating one or more enzymes bound to the complex. In a preferred embodiment, a matrix (M), e.g. solid or semisolid surface or permeable matrix has affixed thereto an enzyme inhibitor-antibody or enzyme inhibitor-antibody immunologically active (inhibitor-binding) fragment of such an antibody (anti I). This insoluble matrix is then contacted with biological fluid, e.g. body fluid, to bind one or more predetermined or suspected enzyme inhibitor-enzyme complexes (I-E) in the biological fluid. The bound enzyme is then detected, identified and preferably quantified.

Enzyme inhibitor (I) as defined for the purpose of this invention and useful in this invention includes naturally occurring plasmin inhibitor and $\alpha_2$ macroglobulin ($\alpha_2$M). It is noted that $\alpha_2$M forms enzyme complexes wherein the enzymatic activity of the enzyme is restricted, but not completely prevented. This latter type of inhibitor is the inhibitor measured in the above disclosed methods. For example, $\alpha_2$M proteinase complexes have been shown to retain hydrolytic activity against low molecular weight substrates, but are almost totally enzymatically nonreactive to large substrates such as proteins.

Methods suitable for detecting and quantifying the bound enzyme are generally known. Generally, after the immobilized E-I-anti I complex has been removed from contact with the biological fluid, the bound enzyme can be reacted in one of two general methods. The first method comprises a reaction with a detection facilitating material which reacts with a site specific to the bound enzyme or enzymes or the bound E-I complex sought and which either has a detectable group or atom measurable by an analytical technique such as a radioactive tag atom, an I.R. or U.V. light absorbing group, or which causes a visible color change; or which generates a detectable cleavage product, a leaving compound or ion, which in turn is measurable by an analytical technique. This class of reaction is not dependent on the enzymatic action of the enzyme which may be biologically inactive in the E-I complex. The second method comprises an enzymatic reaction of the bound enzyme in cases such as $\alpha_2$M, where the bound enzyme retains activity against selected substrates. In such a case the immobilized E-I-anti I complex is contacted with a substrate reactive with the bound enzyme, which substrate upon reaction, by color change or the generation of a readily measurable system-unique cleavage product susceptable to analytic detection, allows analytical determination.

Methods suitable for detecting and quantifying the bound inhibitor antibody in the second general method are also generally known. Generally after an immobilized enzyme anti-body-E, I complex has been removed from contact with the biological fluid, the bound inhibitor in the bound E, I complex is reacted with antibody for said inhibitor which inhibitor antibody has been adapted by modification with a detectable group or atom measurable by an analytical technique such as radioactive tag atom, an I.R. or U.V. light absorbing group or any other measurable phenomenon such as generally described above.

Quantitating the analytical results is generally within the skill of the art. At least one such method comprises quantitating I bound to the E-I-anti I complex so that final quantitation can be expressed as a function of bound inhibitor (I). This can be accomplished by adding a small amount of labeled inhibitor to the biological fluid. The amount of label in the E-I-anti I complex is then measured. This is proportional to the binding of native inhibitor.

Preferably the identification and quantification of the enzyme complexed in the immobilized inhibitor, enzyme complex is carried out in one of two ways. Where the complex is enzymatically active, as $\alpha_2$M, reaction with substrates is employed. For enzyme complexes which are not enzymatically active, antibodies are prepared against the specific enzyme of interest. Thus, for example, antibodies may be prepared in rabbits or goats against the human blood proteinases plasmin, thrombin, kallikrein, C1 (the first component of complement), factor Xa, Hageman factor; or against human pancreatic enzymes trypsin, elastase or chymotrypsin; against human polymorphonuclear leukocyte (white blood cells) neutral proteinases such as elastase, collagenase and cathepsin G; or against proteinase released from damaged tissues such as cathepsin B. Such antibodies have been produced in a number of laboratories.

If desired, the immunoglobulin fraction of the antisera or the specific antibody molecules, isolated for example by affinity chromatography, are then labeled with alkaline phosphatase or other detecting enzyme by methods detailed by Engvall et al., *Immunochemistry*, 8: 871 (1971) and others, or alternatively by use of a radioactive tagging material such as $NaI^{125}$.

The insoluble immunocaptured enzyme, inhibitor complex is then incubated with a specific anti-enzyme antibody such as above, and after a suitable time the unbound antibody is removed by washing. The anti-enzyme antibody remains bound to the enzyme in the immobilized inhibitor complex. The anti-enzyme antibody is then measured for example by determining the activity of the alkaline phosphatase or radioactivity linked to the detecting anti-enzyme antibody. The amount of enzyme bound is quantitated, for example, using standardized curves consisting of purified inhibitor, enzyme complexes. The use of a detecting antibody per se is a known technique which functions well in the context of the immunocapture technique of the invention.

It is pointed out that the biological fluids being surveyed are dynamic systems in which the enzyme balance or content may change due to influences present after the state sought to be measured. To the extent possible, all enzyme or E-I complex altering factors should be avoided by the appropriate selection of reactants and equipment materials. Alternatively, where possible the extraneous enzymatic changes caused during handling and processing can be accounted for and the analytical results appropriately considered or corrected.

One immobilized or insoluble complex comprises (E-I-anti I), i.e. enzyme, enzyme inhibitor and inhibitor antibody or active fragment thereof. In the preferred embodiment the complex is affixed to a solid or semi-solid matrix. The only essential requirement is that the ultimate E-I-anti I complex be immobilized. This may first result only upon the ultimate combination of E or E-I complex with the anti I to form, for example, a precipitate. But preferably an immobilized matrix-anti I entity is preformed and then contacted with biological fluid containing E-I complex. Another possible mode is the addition of anti-I to E-I complex containing biological fluid with the subsequent immobilization, e.g. affixation to a matrix, of the preformed mobile E-I-anti I entity.

The precise nature of the matrix in the method of the invention is not critical beyond the fact that the anti I moiety can be affixed thereto by some means, for example, chemical e.g. covalent bonding or absorption, adsorptions, or the like, in a manner so that the anti I remains reactive with E-I complex. The matrix may be solid or permeable and may be in particulate form; or may comprise, for example, for at least a portion of the structure of a container or be in a unit removably associated with a container.

As to the clotted samples employed in the method of the invention, the preparation of appropriate clotted samples is within the skill of the art and need not be described in detail. Typically, a sufficient amount of a non-interfering clotting agent is added to the plasma sample. The presently preferred clotting agent is Reptilase although other clotting agents will be apparent.

The method of the invention has a number of interesting possible uses. The method obviously provides a useful tool to collect base line data on plasminogen activator levels on apparently healthy persons and persons in known disease states, thus generating a possible diagnostic base. As urokinase-type plasminogen activator has been associated with certain tumors, elevated blood levels may prove early warning of some tumor states. The method of the invention further provides a useful tool to study the effects of a variety of stimuli such as pharmaceuticals, exercise and trauma upon plasminogen activator activity.

BRIEF DESCRIPTION OF THE DRAWINGS

Replicate samples of plasma (0.1 ml) were incubated in plastic tubes with Tris-EDTA buffer or with melanoma tissue plasminogen activator (TPA) (1 or 2 units/ml plasma) in a total vol of 0.19 ml. All samples were clotted with Reptilase (0.01 ml) and incubated at 37° C. A portion (0.07 ml) was removed from each tube at the times indicated on the abscissa and added to EACA-PBS-Tween (1.33 ml). These samples were assayed in triplicate for either $\alpha_2$-plasmin inhibitor-plasmin or $\alpha_2$-macroglobulin-plasmin complexes by the immunosorbent assay. The activity generated in the plasma clotted in the absence of tissue plasminogen activator at each time was substracted from the activity generated in the plasma samples containing the activator. The curves were analyzed by linear regression analysis. For $\alpha_2$-plasmin inhibitor-plasmin complex curves: 2 TPA units (▲—▲; first four data points), $y=159.9x+23.0$ (r=0.989); 1 TPA unit, (△—△), $y=67.5x+9.8$ (r=0.995); spontaneous activity (●—●), $y=28.2x+1.5$ (r=0.997). For $\alpha_2$-macroglobulin-plasmin complex curves: 2 TPA units, $y=62.9x-8.9$ (r=0.995); 1 TPA unit, $y=32.0x-5.3$ (r=0.994); spontaneous activity, $y=5.64x+0.03$ (r=0.996).

Plasmin (0–150 nM) was added to plasma depleted either of $\alpha_2$-plasmin inhibitor (○—○), or of $\alpha_2$-macroglobulin (●—●) by immunoaffinity chromatography. The specific complexes formed between the unabsorbed $\alpha_2$-plasmin inhibitor or $\alpha_2$-macroglobulin and plasmin were measured by the immunosorbent assay (left panel). These curves were used as standards to convert the data shown in FIG. 1 to nM of complexes formed. The sum of the $\alpha_2$-plasmin inhibitor-plasmin and $\alpha_2$-macroglobulin-plasmin complexes generated with time in plasma incubated with buffer or with 1 or 2 units tissue plasminogen activator are shown (right panel). The amount of complexes formed at each time in the plasma without tissue plasminogen activator was subtracted from the amount formed with added activator. For the total plasmin inhibitor-plasmin complexes generated by 2 activator units, $y=35.6x+10.9$ (first 5 points, r=0.995); for 1 unit, $y=15.9x-4.4$ (r=0.986); for 0 units, $y=5.48x-1.3$ (r=0.996).

Plasma (0.2 ml) was mixed with tissue plasminogen activator at 4° C. (left panel: 0.25, 0.5, 1.2, and 4 units/ml plasma; right panel: 6.25, 25, 100 units/ml plasma) in Tris-EDTA-Tween buffer. Either buffer (○—○) or Reptilase (△—△) (0.02 ml) were added to bring the final volume of each mixture to 0.4 ml and the samples were incubated at 37° C. Portions were removed at 0 and 2 h from the mixtures containing the 0.25–4 units/ml, and at 0 and 30 min from those containing the higher concentrations and diluted 1/20 in EACA-PBS-Tween buffer. These samples were assayed for $\alpha_2$-plasmin inhibitor-plasmin complexes. The change in absorbance of the sample obtained at 0 time was subtracted from that of the samples from later times. For the curve generated in Reptilase-clotted plasma (left panel): $y=96.3x+10.3$ (r=0.997); and for that generated in plasma: $y=5.5x-0.06$ (r=0.999).

Urokinase (UK) was added to plasma (0, 2, 4, 8, 12 units/ml plasma) and was incubated with (△—△) or without (●—●) the addition of Reptilase for 2 h at 37° C. Plasma was also incubated with tissue plasminogen activator (TPA) (○—○) and clotted with Reptilase. The generation of $\alpha_2$-plasmin inhibitor plasmin complexes was assayed as described.

Normal plasma (0.2 ml) was incubated with 0, 0.5, 1, 2, 3 or 4 units tissue plasminogen activator/ml plasma diluted in Tris-Tween buffer. The mixtures were clotted with thrombin (0.02 ml) buffer. The mixtures were clotted with thrombin (0.02 ml containing 3 μg thrombin) (△—△) or with Reptilase (0.02 ml; ●—●) and made to a total volume of 0.4 ml with Tris (0.1 M, pH 7.4)-EDTA (0.01 M)-Tween buffer. Alternatively the mixtures were clotted with thrombin and $CaCl_2$ (0.02 M final concentration; ▲—▲). After a 2 h incubation at 37° C., 0.05 ml of the supernate was added to 0.950 l EACA-PBS-Tween. These samples were assayed for $\alpha_2$-plasmin inhibitor-plasmin complexes by the immunosorbent assay. The change in absorbance of the sample without added plasminogen activator was subtracted from those samples with the activator. Curves were fitted by regression analysis. For normal plasma clotted with: Reptilase, $y=139.5x-8.3$, r=0.99; thrombin, $y=86.7x-14.3$, r=0.99; thrombin plus $Ca^{++}$, $y=28.9x-11.4$, r=0.98.

Plasma (0.2 ml) was incubated in duplicate with melanoma tissue plasminogen activator (4 units/ml plasma) at 4° C. or 37° C. The plasma mixtures were clotted with Reptilase (0.02 ml) at 0.5, 1, 1.5 and 2 hrs and incubated for an additional 2 h at 37° C. Samples were removed at the end of this period, diluted 0 1/20 in EACA-PBS-Tween, and assayed for $\alpha_2$-plasmin inhibitor-plasmin complexes by the immunosorbent assay. The results were converted to TPA units using a standard curve. From 1 to 2 hours, there was a significant difference between the plasma incubated at 0° and 37° C. (p<0.0001 by two way analysis of variance). The mean and the SEM are indicated.

Microtitration plates, coated with the IgG fraction of rabbit anti-$\alpha_2$-plasmin inhibitor antiserum (RaPI) are incubated with diluted plasma samples containing plasma inhibitor (PI)-plasmin complexes. After washing, the plates are incubated with the F(ab')$_2$ fragments of rabbit anti-plasmin antibody (Ra plasmin) which has been coupled to alkaline phosphatase (E). A yellow color is then generated by cleavage of the substrate p-nitrophenyl phosphate (pNPP). The color is proportional to the amount of $\alpha_2$-plasmin inhibitor-plasmin complex present.

Figures show mean +SEM with the postocclusion value corrected for the change in hematocrit as described in Methods. "A" shows pre- and post-occlusion values for men (n=7) and "B" for women (n=6). Two-way ANOVA showed that both venous occlusion (F=34.2, p<0.00001) and sex (F=5.9, p=0.02) significantly affected the TPA activity.

Figures represent the mean +SEM with the post-occlusion values corrected for the change in hematocrit as described in Methods. Aspirin did not alter "resting" pre-occlusion TPA concentrations (p=0.3410) but inhibited the rise in TPA concentrations post-occlusion by 69% (p=0.0005).

Percentage inhibition of TPA activity was determined by comparing the increase in each subject's TPA activity induced by venous occlusion after aspirin ingestion to the increase during the control period. There was no significant relationship detected by regression analysis (r=0.3, p=0.16).

Figures represent mean+SEM for the VIII:Rag levels of the 13 subjects with the post-occlusion values corrected for the change in hematocrit as described in Methods. Values are expressed as a percent of normal, pooled human plasma with VIII:Rag concentration equivalent to 100%. Venous occlusion induced a significant rise in VIII:Rag concentration (p=0.0001) while aspirin affected neither pre- nor post-occlusion VIII:-Rag concentrations (p=0.7950).

Two randomly assigned crossover cycles between no drug and ASA (solid lines) or a double-blind cycle between placebo and ASA (dashed line) are shown. Data are expressed as the change in TPA activity in the pre- and post-occlusion venous sample on each occasion, and were obtained by subtracting the pre-occlusion value from the post-occlusion value which had been corrected for the change in hematocrit.

EXAMPLE 1

This study examined the conditions required for the formation of plasmin inhibitor-plasmin complexes in plasma induced by two different classes of plasminogen activators, tissue-type plasminogen activator (TPA) derived from a human melanoma cell line and human urokinase (UK). The results indicate that complex formation in plasma incubated in vitro as measured by an enzyme-linked immunosorbent assay provides a new, sensitive and specific method for the identification and quantification of plasminogen activator activity. The concentration of $\alpha_2$-plasmin inhibitor-plasmin and $\alpha_2$-macroglobulin-plasmin complexes was found to increase in Reptilase-clotted plasma in proportion to the amount of TPA added. A total of 16.9 nM complexes TPA unit $^{-1}$h$^{-1}$ were generated providing a quantitative estimate of the rate of plasmin formation. The generation of complexes by TPA was increased 17-fold in clotted as compared to unclotted plasma whereas clotting had no enhancing effect upon UK-induced complex formation. The rate of TPA-induced complex formation was greater in Reptilase-clotted plasma (15.3 nM unit $^{-1}$h$^{-1}$) than in plasma clotted with thrombin (10.3 nM unit $^{-1}$h$^{-1}$) or with thrombin plus calcium (2.7 nM unit $^{-1}$h$^{-1}$). Incubation of TPA in plasma at 37° C., 0° C. or −70° C. caused a decrease in the generation of complexes subsequently formed following clotting, thereby demonstrating the lability of this activity in plasma. Reptilase-clotted plasma from five subjects generated complexes equivalent to the addition of 0.19±0.06 TPA units ml$^{-1}$ plasma. Venous occlusion of the forearm increased the generation of complexes 6- to 25-fold. The activator induced by venous occlusion had the characteristics of TPA since complexes formed only in clotted plasma. Further, rabbit anti-melanoma TPA inhibited complex-forming activity in TPA-treated as well as in venous stasis plasma but not in UK-treated plasma. These methods provide quantitative techniques for the further definition of biochemical events involved in activation of the fibrinolytic enzyme pathway.

To define the mechanisms of complex formation in vivo, the generation of plasmin inhibitor-plasmin complexes in plasma by both tissue-type plasminogen activator from a human melanoma cell line and urokinase has been examined under a variety of experimental conditions. The findings indicate that the rate of formation of these complexes depends upon the type of plasminogen activator added, whether fibrin is present and which coagulant enzyme is used. Measuring the generation of $\alpha_2$-plasmin inhibitor-plasmin complexes preferably in Reptilase-clotted plasma has proven to be a sensitive and specific method for the quantification and characterization of blood plasminogen activator activity in vivo. The studies have demonstrated a six- to twenty five-fold increase in the rate of formation of $\alpha_2$-plasmin inhibitor-plasmin complexes in plasma from five normal individuals obtained following venous occlusion. These methods have been utilized to assess the stability of this endogenous plasminogen activator activity in plasma and to compare its immunologic reactivity to melanoma tissue plasminogen activator. These studies clarify the mechanisms by which plasmin inhibitor-plasmin complexes are formed. They also illustrate a new approach to the study of the fibrinolytic enzyme pathway.

Abbreviations used in this example: PBS-Tween, phosphate-buffered saline, containing Tween; EACA-PBS-Tween, phosphate-buffered saline containing Tween and epsilon amino caproic acid; TPA, tissue plasminogen activator; UK, urokinase; DDAVP, 1-desamino-8-D-arginine vasopressin.

EXPERIMENTAL PROCEDURES

Blood samples. Venous blood was drawn into plastic syringes from volunteers after minimum venous stasis and added to 3.8% sodium citrate (9:1, vol/vol). Blood was also obtained following venous occlusion of the forearm by a sphygmomanometer cuff inflated to 20 mm Hg below systolic pressure for 10 min just prior to release of pressure from the cuff. Informed consent was obtained using a protocol approved by the Human Experimentation Committee. The plasma, harvested following centrifugation at 2,500 rpm for 10 min, was utilized within 30 min of venipuncture or was frozen in plastic tubes at −70° C.

Purification of tissue plasminogen activator and of plasma proteins. Human melanoma cell tissue plasminogen activator was prepared by minor modifications of previously described methods; [Rijken et al., J. Biol. Chem., 256: 7035-7041 (1979)]. The specific activity of the final product was 100,000 units/mg. The activator was stored at a concentration of 1550 units/ml at −70° C. The fibrinolytic activity of the melanoma tissue plasminogen activator was determined by the $^{125}$I-fibrin plate assay as detailed previously; [Unkeless et al., J. Exptl. Med., 137: 85-111 (1973)] and standardized by comparison with urokinase (abbokinase). Antisera were raised in rabbits using melanoma plasminogen activator that was purified by electrophoresis on a preparative 9% polyacrylamide gel under non-reducing conditions; [Rohrlich et al., J. Cell. Physiol., 109: 1-15 (1981)].

$\alpha_2$-plasmin inhibitor and $\alpha_2$-macroglobulin were purified as previously detailed; [Wiman, Biochem. J., 191: 229-232 (1980); Harpel, Methods Enzymol., 45: 639-652

(1976)]. Plasminogen was isolated from fresh plasma by lysine affinity chromatography 5 [Deutsch et al., *Science*, 170: 1095–1096 (1970)] in the presence of soybean trypsin inhibitor (100 ug/ml plasma, Worthington), which was followed by gel filtration chromotography (Bio-gel A-0.5 m, Bio-Rad Laboratories, Richmond, Calif.). The concentration of each protein was determined by its extinction coefficient ($\alpha_2$-plasmin inhibitor=7.03, [Moroi et al., *J. Biol. Chem.*, 251: 5956–5965 (1976)] $\alpha_2$-macroglobulin=8.93, [Hall et al., *Biochem. J.*, 171: 27–38 (1978)]; plasminogen=17.0, [Robbins et al., *Methods Enzymol.*, 19: 184–199 (1970)].

Plasmin was prepared by the activation of plasminogen with insolubilized urokinase as described previously; [Harpel, *J. Clin. Invest.*, 68: 46–55 (1981)]. The activity of the plasmin was determined by active site titration; [Chase et al., *Methods Enzymol.*, 19: 20–27 (1970)]. The plasmin was stored at $-70°$ C. in 50% glycerol, at a concentration of 2.0 mg/ml active enzyme.

Figure 2:
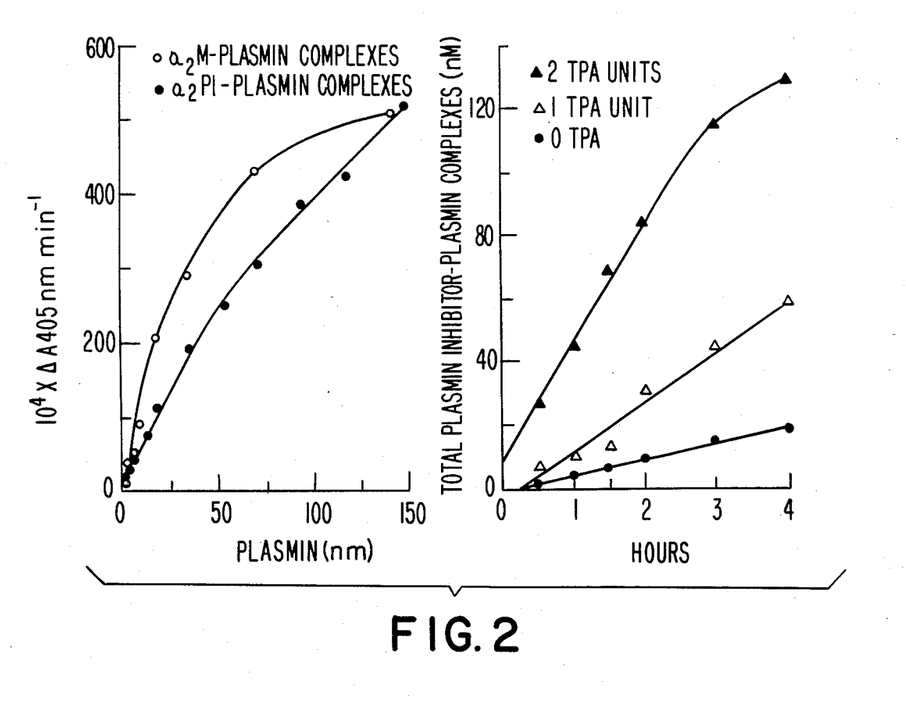
FIG. 2. Quantification of plasmin inhibitor-plasmin complexes formed in plasma.

$\alpha_2$-plasmin inhibitor-plasmin and $\alpha_2$-macroglobulin-plasmin complex standard curves in plasma as measured by the enzyme-linked immunosorbent assay. Plasma was depleted of either $\alpha_2$-plasmin inhibitor or $\alpha_2$-macroglobulin by immunoaffinity chromatography using the IgG fraction of the respective rabbit antisera that was coupled to BioGel A-5m (BioRad Laboratories); [Harpel, *J. Clin. Invest.*, 68: 46–55 (1981)]. The change in absorbance per minute was plotted against the concentration of plasmin. Since the molar combining ratio of plasmin with its inhibitors is one, the concentration of plasmin added is equivalent to the concentration of complex formed. The curves produced (FIG. 2, left panel), therefore, were used as standards to quantify the complexes generated in plasma (FIG. 2, right panel).

Generation of inhibitor-plasmin complexes in plasma by the addition of plasminogen activators. Plasma was mixed with Tris (0.1 M)-HCl buffer, pH 7.4, containing disodium EDTA (0.01 M) and as indicated in the Figure legends (e.g. FIGS. 3 and 4), varying concentrations of melanoma tissue plasminogen activator or of urokinase diluted in Tris (0.1 M), pH 7.4, containing Tween 20 (0.05%) were added. The mixtures were incubated in 1.5 ml Eppendorf Tubes at 37° C. with or without the addition of Reptilase (0.1 ml/ml plasma, reconstituted according to the manufacturers instructions, Abbott Laboratories, Chicago, Ill.) or of human $\alpha$-thrombin (0.1 ml/ml plasma containing 15 $\mu$g thrombin). The final volume of the plasma mixture achieved a ½ dilution of the starting plasma. At varying intervals as indicated in the Figures (e.g FIGS. 3 and 4), the tubes were centrifuged 1 min (Eppendorf Micro Centrifuge, Brinkman Inst., Inc.). The supernatants were diluted 1/20 in EACA-PBS-Tween buffer. These samples were frozen at $-20°$ C. and assayed subsequently for either $\alpha_2$-plasmin inhibitor-plasmin or $\alpha_2$-macroglobulin-plasmin complexes by the immunosorbent assay.

The stability of melanoma plasminogen activator was studied by adding the activator to plasma and freezing portions at $-70°$ C. for 72 hrs. The thawed samples were diluted 1/20 in EACA-PBS-Tween, clotted with Reptilase and incubated for 2 h at 37° C. The production of $\alpha_2$-plasmin inhibitor-plasmin complexes was measured as described. The fresh plasma-tissue plasminogen activator mixture was assayed immediately in a similar manner. The change in absorbance per minute was converted to tissue plasminogen activator units utilizing the curve of FIG. 3, left panel. In other studies, plasma containing added tissue plasminogen activator was incubated in an ice bath or at 37° C. and portions were removed at intervals, diluted in EACA-PBS-Tween, clotted with Reptilase, and incubated at 37° C. for 2 h. The supernatant was assayed for the formation of $\alpha_2$-plasmin inhibitor-plasmin complexes. Plasma also was incubated for 2 h at 37° C. following which tissue plasminogen activator and Reptilase were added. This plasma did not show a significant loss in its capacity to support the formation of $\alpha_2$-plasmin inhibitor-plasmin complexes as compared to unincubated plasma.

In these studies the curves of best fit were calculated using the family regression curve analysis package supplied by Hewlett-Packard and a Hewlett-Packard model 9815A calculator with a model 9862A X-Y plotter (Hewlett-Packard Co., Palo Alto, Calif.).

Studies of the generation of inhibitor-plasmin complexes in plasma obtained before and following venous occlusion. Blood was obtained before and after 10 min of venous occlusion of the forearm in five normal men. The plasma or Reptilase-clotted plasma was incubated 2 h at 37° C. as detailed in Table I and the formation of $\alpha_2$-plasmin inhibitor-plasmin complexes measured. The stability of the venous occlusion-induced plasminogen activator activity was examined by incubating the post occlusion plasma at 37° C. and sampling portions at 0, 30, 120 min for the generation of $\alpha_2$-plasmin inhibitor-plasmin complexes following clotting with Reptilase.

TABLE I

Generation of $\alpha_2$-plasmin Inhibitor-Plasmin Complexes in Incubated, Reptilase-Clotted Plasma from Pre- and Post-occlusion Venous Blood.

| Subject | Pre-occlusion plasma[a] | Post-occlusion plasma |
|---|---|---|
| | TPA units/ml plasma | |
| A | 0.21 | 2.31 |
| B | 0.12 | 3.02 |
| C | 0.18 | 1.13 |
| D | 0.17 | 2.69 |
| E | 0.29 | 4.93 |

[a]Pre-occlusion blood was obtained after minimum venous stasis. Post-occlusion blood was obtained in the opposite arm following 10 min occlusion with a blood pressure cuff inflated to 20 mm Hg below systolic pressure. In the assay, the blood was centrifuged within 10 min. after venipuncture, and the plasma, maintained at 4° C. was tested within 30 min. Plasma (0.2 ml) was incubated in duplicate with Tris-EDTA buffer (0.2 ml) or with buffer (0.18 ml) and Reptilase (0.02 ml) at 37° C. Samples were removed at 0 and 2 h, diluted 1/20 with EACA-PBS-Tween buffer and then assayed for $\alpha_2$-plasmin inhibitor-plasmin complexes as indicated in the "Experimental Procedures". The change in absorbance of the 2 hr value minus the 0 h sample was converted to tissue plasminogen activator units using a curve similar to FIG. 2, left panel, produced by adding increasing amounts of TPA to the subjects own pre-occlusion plasma followed by clotting with Reptilase. Since hemoconcentration occurred during the 10 min of venous occlusion, the post-occlusion activity was corrected by multiplying the calculated TPA concentration by the formula: 1-post-occlusion hematocrit/1-pre-occlusion hematocrit.

The relationship of melanoma tissue plasminogen activator to the activator activity induced by venous occlusion was studied in the $\alpha_2$-plasmin inhibitor-plasmin complex forming assay. As detailed in Table II, post venous occlusion plasma, or plasma to which tissue plasminogen activator or urokinase was added was incubated 30 min with the IgG fraction of rabbit anti-melanoma tissue plasminogen activator antisera or with the IgG fraction of serum from an unimmunized rabbit. The plasma was clotted with Reptilase, a 0 time sample obtained, and incubated an additional 2 h at 37° C. The formation of complexes was determined by the immunosorbent assay. To test the activity of rabbit anti-melanoma tissue plasminogen activator antisera against urokinase, the IgG fraction was preincubated with urokinase, as indicated in Table II, prior to the addition of plasma that was then clotted with Reptilase and incubated 2 h at 37° C.

TABLE II

Effect of Rabbit Anti-Tissue Plasminogen Activator Antibody on Plasminogen Activator Activity in Plasma Incubated with Tissue Plasminogen Activator, Urokinase, or in Plasma Obtained following Venous Occlusion.

| Incubation Mixture[a] | | % Activity |
|---|---|---|
| | TPA units[b] | |
| TPA (4U)-plasma | 2.0 ± .02 | 100 |
| TPA + RaTPA | 0.09 ± .006 | 4.5 |
| TPA + IgG | 1.75 ± .013 | 87.5 |
| TPA (2U)-plasma | 0.78 ± .01 | 100 |
| TPA + RaTPA | 0.02 ± .07 | 2.6 |
| TPA + IgG | 0.72 ± .012 | 92.3 |
| Stasis plasma | 0.94 ± .02 | 100 |
| Stasis + RaTPA | 0.02 ± .01 | 2.1 |
| Stasis + IgG | 0.89 ± .01 | 94.7 |
| | UK units | |
| UK-plasma | 4.0 ± .32 | 100 |
| UK + RaTPA | 3.6 ± .25 | 90 |
| UK + IgG | 3.5 ± .06 | 87.5 |

[a]Plasma (0.2 ml) was preincubated in duplicate with either 0.8 or 0.4 units TPA (TPA-plasma) with and without 80 μg of the IgG fraction of rabbit anti-melanoma plasminogen activator (TPA-plasma + RaTPA) or with normal rabbit IgG (TPA-plasma + IgG) diluted in Tris-EDTA buffer for 30 min at 25° C. in a total volume of 0.38 ml. Reptilase (0.02 ml) was added and the mixture incubated for 2 h at 37° C. Samples were taken following Reptilase addition at 0 and 2 h and diluted 1/20 in EACA-PBS-Tween buffer for assay for $\alpha_2$-plasmin inhibitor-plasmin complexes. Alternatively, plasma was obtained from blood collected following 10 min of venous occlusion of the forearm (stasis plasma) and incubated with buffer or with 80 μg of rabbit anti-melanoma plasminogen activator or with normal rabbit IgG and processed as detailed above. To test for the effect of the anti-melanoma antibody against urokinase (UK), 80 μg of rabbit anti-melanoma plasminogen activator IgG or normalrabbit IgG were preincubated with UK (0.8 units) 30 min at 25° C. Plasma (0.2 ml) was added to the mixture that was then clotted with Reptilase (0.02 ml) in a total volume of 0.4 ml and incubated 2 h at 37° C. Samples were obtained as described above for ELISA.
[b]The change in absorbance in the ELISA for $\alpha_2$-plasmin inhibitor-plasmin complexes was converted to TPA units using a standard curve. A similar curve was constructed for converting the ELISA values to urokinase units.

RESULTS

Figure 1:
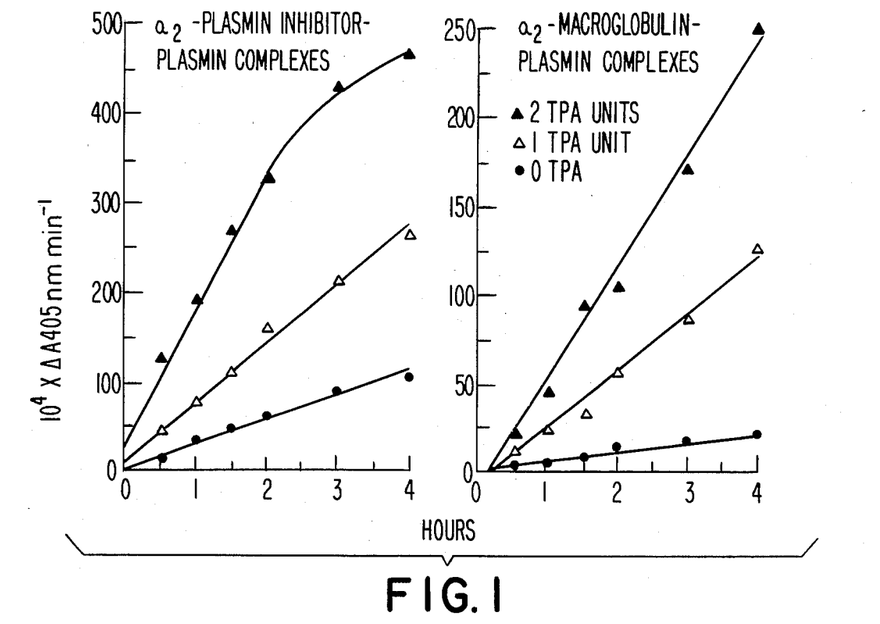
FIG. 1. Time-dependent generation of $\alpha_2$-plasmin inhibitor-plasmin and $\alpha_2$-macroglobulin-plasmin complexes in Reptilase-clotted plasma by tissue plasminogen activator.

Generation of $\alpha_2$-plasmin inhibitor or $\alpha_2$-macroglobulin-plasmin complexes in plasma by melanoma cell tissue plasminogen activator. Melanoma tissue plasminogen activator (1 or 2 units/ml plasma) or buffer were added to plasma, the mixtures clotted with Reptilase and incubated at 37° C. (FIG. 1). At varying intervals the tubes were centrifuged and the supernatants diluted in EACA-PBS-Tween buffer and assayed for the formation of $\alpha_2$-plasmin inhibitor-plasmin and $\alpha_2$-macroglobulin-plasmin complexes by the differential antibody enzyme-linked immunosorbent assay. The change in absorbance in the assays for both types of inhibitor-enzyme complexes increased linearly with time and the rate of formation of these complexes was dependent upon the concentration of tissue plasminogen activator added.

Standard curves were prepared for the conversion of the absorbance values to nM complexes formed by adding increasing concentrations of plasmin to plasma depleted of either $\alpha_2$-plasmin-inhibitor or $\alpha_2$-macroglobulin by immunoaffinity chromatography (FIG. 2, left panel). From these curves the amount of complex formed at each time point in FIG. 1 was determined and the sum of the $\alpha_2$-plasmin inhibitor-plasmin and $\alpha_2$-macroglobulin-plasmin complexes formed was plotted (FIG. 2, right panel). In the plasma clotted without added exogenous plasminogen activator, a total of 5.5 nM complexes $h^{-1}$ were generated. For the plasma clotted in the presence of 1 or 2 units of tissue activator, 15.9 and 35.6 nM complexes $h^{-1}$ were formed with a mean of 16.9 nM TPA unit$^{-1}h^{-1}$. Analysis of the distribution of plasmin between its two inhibitors at each time point demonstrated that 85% was bound to $\alpha_2$-plasmin inhibitor and the remainder to $\alpha_2$-macroglobulin.

Figure 3:
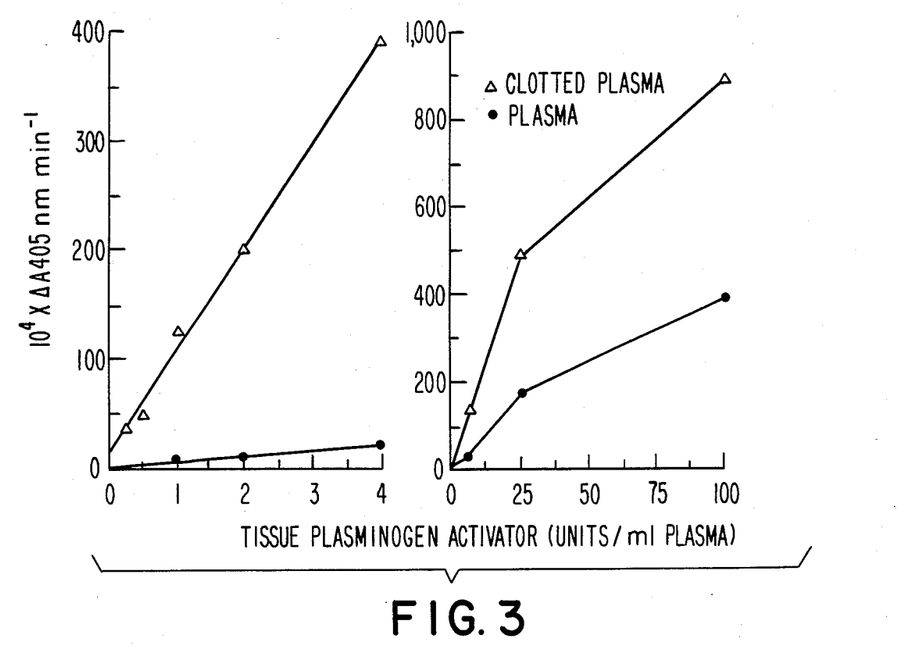
FIG. 3. Comparison of the generation of $\alpha_2$-plasmin inhibitor-plasmin complexes by varying concentrations of tissue plasminogen activator in plasma or clotted plasma.

The effect of clotting plasma with Reptilase on the generation of $\alpha_2$-plasmin inhibitor-plasmin complexes by tissue plasminogen activator was compared to non-Reptilase clotted plasma (FIG. 3). When concentrations of tissue plasminogen activator from 0.25 to 4.0 units/ml plasma were added, a large difference in the generation of $\alpha_2$-plasmin inhibitor-plasmin complexes was observed between the clotted and unclotted samples (FIG. 3, left panel). Inhibitor-enzyme complexes were just detectable in the plasma incubated for 2 hours at 37° C. However, when plasma was clotted with Reptilase, there was a 17-fold increase in the formation of complexes at these same concentrations of tissue plasminogen activator. When higher concentrations of tissue plasminogen activator were used (FIG. 3, right panel) the differences between enzyme-inhibitor complexes formed in clotted and unclotted plasma were less. The rate of formation of complexes in Reptilase-clotted plasma was about four-fold higher than in unclotted plasma.

Figure 4:
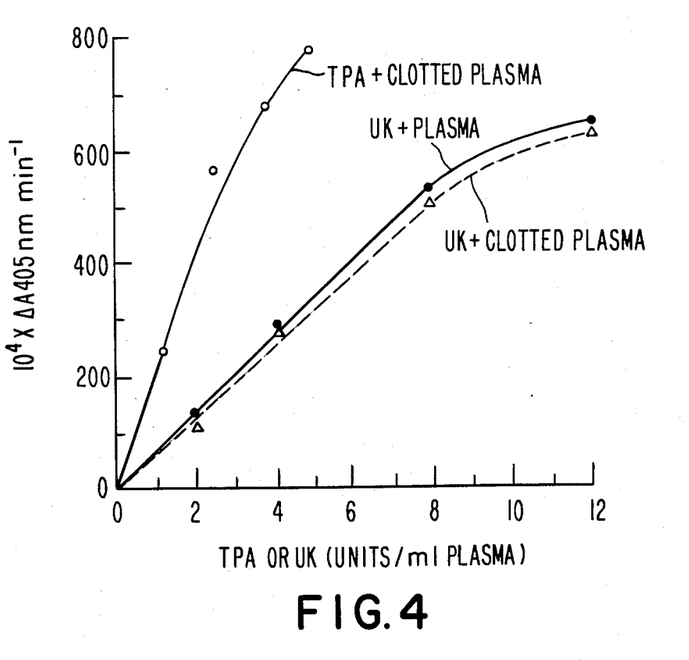
FIG. 4. Generation of $\alpha_2$-plasmin inhibitor-plasmin complexes by urokinase in plasma or clotted plasma and comparison with tissue plasminogen activator.

The capacity of urokinase to induce formation of $\alpha_2$-plasmin inhibitor-plasmin complexes was studied in Reptilase-clotted and unclotted plasma (FIG. 4). In contrast to the accelerating effect of fibrin on formation of complexes demonstrated for tissue plasminogen activator, no significant difference in the production of complexes by urokinase was observed in plasma, regardless of whether the plasma was clotted with Reptilase. The $\alpha_2$-plasmin inhibitor-plasmin complex generating activity of urokinase was compared to that of tissue plasminogen activator. This was feasible since the activity of the melanoma tissue plasminogen activator had been established against a urokinase standard using a $^{125}$I-fibrin plate assay. Comparison of the complex forming activity of these two different plasminogen activators in Reptilase-clotted plasma indicated that approximately 3 units of urokinase were required to produce the equivalent complex forming activity of one unit of tissue plasminogen activator. In the experiment shown (FIG. 4), the plasma used was from a different donor than in prior experiments, and somewhat more complex forming activity for a given amount of tissue plasminogen activator was observed. The results shown in FIG. 4 were confirmed using several different plasma which demonstrated variable rates of complex formation by tissue plasminogen activator.

Figure 5:
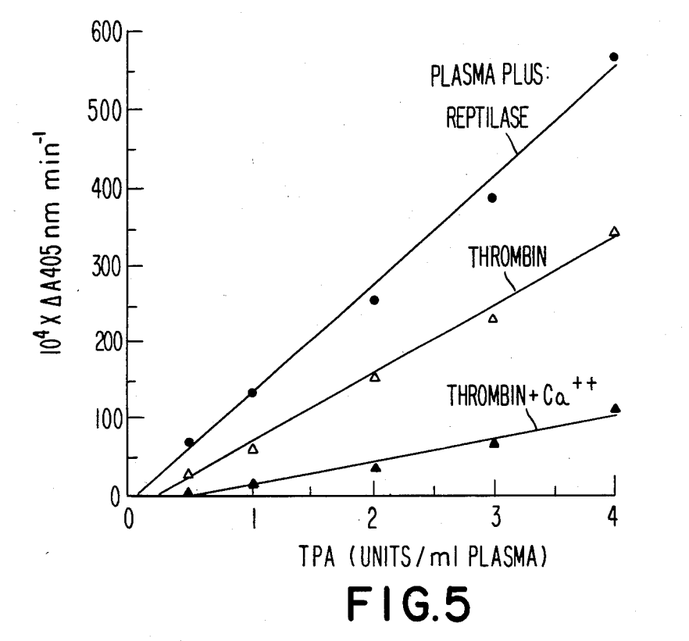
FIG. 5. Effect of Reptilase, thrombin or thrombin with $Ca^{++}$ on the tissue plasminogen activator-induced generation of $\alpha_2$-plasmin inhibitor-plasmin complexes in plasma.

Comparison of the effect of clotting plasma with Reptilase, thrombin or thrombin with calcium on the generation of $\alpha_2$-plasmin inhibitor-plasmin complexes by tissue plasminogen activator. The rate of formation of $\alpha_2$-plasmin inhibitor-plasmin complexes by tissue plasminogen activator was influenced by the specific coagulant enzyme added to plasma (FIG. 5). Significantly less complex generation occurred when human thrombin rather than Reptilase was used to clot the plasma sample in the presence of varying concentrations of tissue plasminogen activator. Approximately 1.7 times more tissue plasminogen activator was required to yield the same change in absorbance in thrombin-clotted as in Reptilase-clotted plasma. To facilitate comparison of the effect of the different coagulant enzymes, the data in FIG. 5 were converted to nM $\alpha_2$-plasmin inhibitor-plasmin complex using the standard curve in FIG. 2, left panel. In Reptilase-clotted plasma, 15.3 nM TPA unit$^{-1}$h$^{-1}$ of complexes were generated as compared to 10.3 nM unit$^{-1}$h$^{-1}$ in thrombin-clotted plasma representing a 33% decrease in activity. The addition to plasma of calcium chloride and thrombin produced 2.7 nM unit$^{-1}$h$^{-1}$ representing an 82.3% decrease in the generation of $\alpha_2$-plasmin inhibitor-plasmin complexes by tissue plasminogen activator in comparison to the Reptilase-clotted sample.

Figure 6:
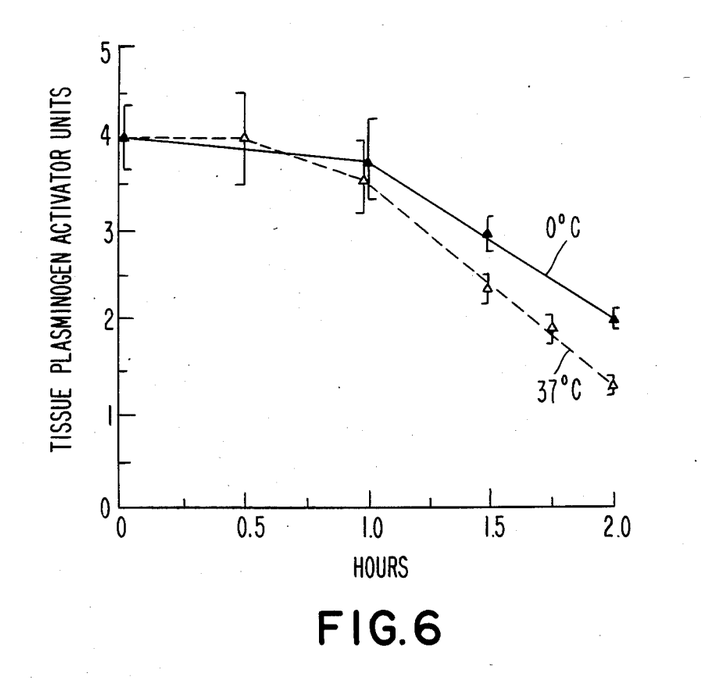
FIG. 6. Stability of tissue plasminogen activator incubated in plasma prior to clotting.

Stability of tissue plasminogen activator in plasma. Tissue plasminogen activator (4 units) was preincubated with plasma for varying periods either at 0° or 37° C. prior to clotting with Reptilase, and the generation of $\alpha_2$-plasmin inhibitor-plasmin complexes was followed (FIG. 6). The activity of the activator remained relatively stable at both temperatures for the first hour, then fell in a linear fashion. The decay of activator was significantly greater at 37° than at 0°, falling to 1.36 units (34% of the starting activity) at 2 hours of incubation. At 0° C. the activity at 2 hours fell to 2.1 units (52.5% of the starting activity). Tissue plasminogen activator incubated for 2 hours with buffer, either at 37° or 0° C., and then tested for $\alpha_2$-plasmin inhibitor-plasmin forming activity in the Reptilase-clotted plasma demonstrated no loss of activity.

Tissue plasminogen activator was also labile in plasma when frozen at −70° C. (Table III). Freezing caused a 30% loss of the endogenous plasminogen activator activity in normal resting plasma. When tissue plasminogen activator was added to plasma that was subsequently frozen, a somewhat greater loss (48 and 67%) of plasminogen activator activity was observed.

TABLE III

Effect of Freezing on Tissue Plasminogen Activator Activity as Measured by the $\alpha_2$-Plasmin Inhibitor-Plasmin Complex Generating Assay

| Plasma plus[a]: | Time (−70° C.) | TPA units[b] | % Activity |
|---|---|---|---|
| Buffer | 0 | 0.30 ± 0.005 | 100 |
| | 72 h | 0.21 ± 0.01 | 70 |
| TPA (0.5 U) | 0 | 0.51 ± 0.015 | 100 |
| | 72 | 0.24 ± 0.01 | 48 |
| TPA (2.0 U) | 0 | 2.0 ± 0.09 | 100 |
| | 72 | 1.33 ± 0.08 | 67 |

[a]Tissue plasminogen activator (TPA), or Tris-Tween buffer was added to plasma. Portions of these mixtures were frozen at −70° C. The fresh sample (0.2 ml) was clotted with Reptilase in a final plasma dilution of ½ in Tris-EDTA buffer. 0 and 2 h samples were diluted 1/20 in EACA-PBS-Tween and assayed for $\alpha_2$-plasmin inhibitor-plasmin complexes. After 72 hours, the frozen samples were thawed at 37° C. and assayed similarly.
[b]The concentration of $\alpha_2$-plasmin inhibitor-plasmin complexes as determined by ELISA was converted to TPA units using a standard curve (FIG. 3, left panel). Comparison of each sample at 0 time with 72 hours yields a P < 0.001. The spontaneous TPA activity demonstrated in the plasma-buffer mixture was substracted from the activity generated when exogenous TPA was added to plasma. The mean and the SEM are indicated.

Effect of venous occlusion on the generation of $\alpha_2$-plasmin inhibitor-plasmin complexes in incubated plasma. Plasma was harvested from blood collected prior to and following 10 min of forearm venous occlusion at 20 mm Hg below systolic blood pressure in five individuals. The plasma, maintained at 4° C., was tested within 30 minutes of venipuncture for the formation of $\alpha_2$-plasmin inhibitor-plasmin complexes after a 2 hour incubation at 37° C. with or without clotting with Reptilase (Table I). No plasma generated complexes either before or after venous occlusion in the absence of clotting with Reptilase. In the clotted preocclusion plasma, the concentration of complexes formed when converted to tissue plasminogen activator units, yielded a mean of 0.19±0.06 units. In the post-occlusion samples the increase in activity observed ranged from 6- to 25-fold, the mean being 2.81±1.38 units.

To test the stability of the plasminogen activator activity induced by venous occlusion, plasma obtained following stasis was incubated for 30 and 120 min at 37° C. prior to clotting with Reptilase (Table IV). The ability to generate $\alpha_2$-plasmin inhibitor-plasmin complexes declined with time, to approximately 23% of the starting activity in the plasma sample clotted without incubation.

TABLE IV

Effect of Incubation on Plasminogen Activator Activity in Plasma Obtained from Post-Venous Occlusion Blood[a]

| Time | TPA units | % Activity |
|---|---|---|
| 0 min | 2.50 ± .10 | 100 |
| 30 | 1.50 ± .05 | 60 |
| 120 | 0.58 ± .02 | 23 |

[a]Post-occlusion plasma (0.2 ml) was incubated in duplicate with 0.18 ml Tris-EDTA buffer for 0, 30 and 120 min at 37° C. Reptilase (0.02 ml) was added, and the mixtures incubated for an additional 2 hr. Samples were removed at 0 and 2 h following Reptilase addition and diluted 1/20 in EACA-PBS-Tween. These samples were tested for $\alpha_2$-plasmin inhibitor-plasmin complex activity by ELISA, and the results expressed in TPA units by reference to a standard curve.

Effect of rabbit anti-human melanoma plasminogen activator on the generation of $\alpha_2$-plasmin inhibitor-plasmin complexes in tissue plasminogen activator-treated plasma, in post venous occlusion plasma and urokinase-treated plasma. Plasma to which two different concentrations of tissue plasminogen activator were added, or plasma obtained following 10 min venous occlusion was incubated 30 min with buffer, with the IgG fraction of rabbit anti-human melanoma plasminogen activator or with normal rabbit IgG prior to clotting with Reptilase (Table II). The antibody directed against the tissue activator almost completely inhibited the complex forming activity of tissue activator treated-plasma and of post-venous occlusion plasma while normal rabbit IgG had no effect. In contrast, the rabbit anti-melanoma plasminogen activator antibody did not inhibit urokinase (Table II).

The above study characterizes and quantifies plasminogen activation in plasma by measuring the generation of the complexes that form between plasmin and its two plasma inhibitors, $\alpha_2$-plasmin inhibitor and $\alpha_2$-macroglobulin. It has been possible to measure resting levels of blood plasminogen activator activity in normal individuals and to quantify and further characterize the increased levels of plasminogen activator activity stimulated by venous occlusion of the forearm.

A time-dependent, linear increase in the concentration of both $\alpha_2$-plasmin inhibitor and $\alpha_2$-macroglobulin-plasmin complexes in plasma clotted with Reptilase, serves as the basis for this invention. Conversion of the change in absorbance in the immunosorbent assay for the two types of inhibitor complexes measured using standard curves (FIG. 2, left panel), permitted quanitification of both the distribution of the plasmin formed between its two inhibitors, and the total concentration of complexes formed (FIG. 2, right panel). Approximately 85 percent of the bound plasmin was in complex with $\alpha_2$-plasmin inhibitor and the remainder was bound to $\alpha_2$-macroglobulin. These percentages remained relatively constant with time thus supporting previous findings with urokinase, that both types of inhibitor-plasmin complexes form simultaneously in plasma, although at different rates [Harpel, J. Clin. Invest., 68: 46–55 (1981)]. It can be determined from the slopes of the curves in FIG. 2, (right panel), that a total of 16.9 nM of complexes/unit tissue activator/h are generated, thus providing a quantitative estimate of the amount of plasmin generated in Reptilase-clotted plasma.

Fibrin catalyzes the activation of plasminogen by tissue activator [Camiolo et al., *Proc. Soc. Exp. Biol. Med.*, 38: 277-280 (1971); Thorsen et al., *Thromb. Diath. Haemorrh.*, 28: 65-74 (1972); Wallen, *Progress in Chemical Fibrinolysis and Thrombolysis*, Davidson et al., eds., Vol. 3, pp. 167-181 (1978), Raven Press, New York; Hoylaerts et al., *J. Biol. Chem.*, 257: 2912-2919 (1982)] and the present study demonstrates that the tissue plasminogen activator-induced generation of $\alpha_2$-plasmin inhibitor-plasmin complexes in plasma is also accelerated by the presence of fibrin. At plasma concentrations of tissue plasminogen activator from 0.25 to 4.0 units per ml plasma, there is an increase in $\alpha_2$-plasmin inhibitor-plasmin complexes in both clotted and unclotted plasma that is proportional to the amount of activator added. However, the rate of formation of complexes is enhanced approximately seventeen-fold in the Reptilase-clotted samples (FIG. 3). At higher concentrations of tissue plasminogen activator, 25 to 100 units per ml plasma, there was less difference between the generation of $\alpha_2$-plasmin inhibitor-plasma complexes in clotted versus unclotted plasma, however a four-fold stimulatory effect of fibrin was still apparent. These data parallel the kinetic analysis by Hoylaerts et al., supra, of the activation of glu-plasminogen by melanoma plasminogen activator in purified systems.

In contrast to these observations on tissue plasminogen activator, clotting plasma with Reptilase failed to enhance the generation of $\alpha_2$-plasmin inhibitor-plasmin complexes by urokinase (FIG. 4). These results in plasma are consistent with prior studies that demonstrate that fibrin does not affect the activation of plasminogen by urokinase in purified systems; Camiolo et al., supra; Thorsen et al., supra; Wallen, supra. In the present study urokinase was found to be about threefold less effective in inducing the formation of plasmin inhibitor-enzyme complexes in plasma when compared to the complex-forming activity of tissue plasminogen activator in clotted plasma. These results are consistent with the stimulatory effect of fibrin on the activation of plasminogen by tissue plasminogen activator and correlate with the observation that tissue activator has a higher fibrinolytic and a lower fibrinogenolytic activity than urokinase [Matsuo et al., *Thromb. Haemostas.*, 45: 225-229 (1981)]. The difference in complex forming activity of the two types of plasminogen activators may also reflect the inhibitory activity of the several different plasma proteinase inhibitors that form complexes with urokinase in plasma; [Clemmensen et al., *Biochem. Biophys. Acta.*, 429: 591-599 (1976); Clemmensen, *Thrombos. Haemostas.*, 39: 616-623 (1978); Vahtera et al., *Biochem. J.*, 171: 767-770 (1978); Murano et al., *Blood*, 55: 430-436 (1980)]. In contrast, tissue plasminogen activator, bound to the fibrin clot may be protected from its plasma inhibitors that appear to react slowly with the activator; [Korninger et al., *Thromb. Haemostas.*, 46: 662-665 (1981)].

A comparison of the effect of Reptilase, isolated from the venom of Bothrops atrox, that cleaves fibrinopeptide A from fibrinogen, and thrombin which cleaves both fibrinopeptides A and B from fibrinogen, indicates that significantly more complexes were formed when the tissue activator-treated plasma was clotted with Reptilase than with thrombin. These results extend the observations of Ranby, Wallen and Bergsdorf, [Ranby et al., *Thrombos. Haemostas.*, b 46: 12 (abstr.) (1981)], who have observed in purified systems that the activation of plasminogen by tissue activator is increased five-fold in the presence of Reptilase-clotted fibrinogen as compared to thrombin-clotted fibrinogen. The addition of calcium chloride to the solution containing thrombin produced a decrease in the tissue activator-induced generation of $\alpha_2$-plasmin inhibitor-plasmin complexes in plasma as compared to thrombin alone. This inhibitory effect of calcium on the fibrinolytic enzyme system has been noted previously [Fearnley, *Fibrinolysis*, pp. 148-150, (1965), Williams & Wilsins Co., Baltimore; Tran-Thang et al., *Thrombos Haemostas.*, 46: 113 (abstr.) (1981)] and has been ascribed to the resistance of fibrin-stabilizing factor catalyzed cross-linked fibrin clots to digestion by plasmin; [Lorand et al., *Nature*, 195: 911-912 (1962); Gormsen et al., *Arch. Biochem. Biophys.*, 120: 654-665 (1967); Henderson et al., *Br. J. Haematol.*, 17: 445-453 (1969); McDonagh et al., *Br. J. Haemat.*, 21: 323-332 (1971); Gaffney et al., *Thromb. Res.*, 14: 85-94 (1979)]. Other studies, using purified fibrin rather than fibrin clots derived from plasma, have failed to demonstrate differences in resistance to lysis between cross-linked and non cross-linked clots; [Haverkate, *Thromb. Diath. Haemorrh.*, 34: 584 (abstr.) (1975); Rampling, *Thromb. Res.*, 12: 287-295 (1978)]. Aoki and his coworkers [Sakata et al., *J. Clin. Invest.*, 65: 290-297 (1980); Sakata et al., *J. Clin. Invest.*, 69: 536-542 (1982); Tamaki et al., *J. Biol. Chem.*, 257: 14767-14772 (1982)] have partially resolved these discrepancies by their demonstration that $\alpha_2$-plasmin inhibitor is covalently linked to fibrin by fibrin-stabilizing factor following activation by thrombin and calcium. They postulated that this cross-linking of the inhibitor produced fibrin clots resistant to plasmin-induced fibrinolysis by increasing the local concentration of $\alpha_2$-plasmin inhibitor as well as by masking plasminogen binding sites on fibrin. These mechanisms may also explain the apparent inhibitory effect of calcium on the generation of plasmin inhibitor-plasmin complexes observed in the present study.

EXAMPLE 2

This example demonstrates that aspirin serves as a pharmacologic modulator of intravascular fibrinolytic activity and that the method of the invention effectively monitors its action.

Protocol

Informed consent was obtained from healthy, human volunteers for participation in this study as approved by the Human Experimentation Committee. Subjects were randomly assigned to a first study period during which they ingested either aspirin or no drug. If assigned to the aspirin group, subjects ingested 650 mg of aspirin (Hudson Pharmaceutical Corp., West Caldwell, NY), both 18 h and 2 h before blood collection. Aspirin was given to subjects after determining that tablets from that lot flocculated and broke up completely within 15 sec in water brought to pH 3 by the addition of 0.1 N HCl. Subjects underwent venipuncture as described below and returned after 10 days during which no aspirin was ingested. For the second study, subjects took whatever they had not received in the first study (i.e. aspirin or no drug).

One subject also participated in a randomized, doubleblind, crossover trial during which he received either pulverized aspirin 650 mg (Hudson) or lactose powder in a #0 gelatin capsule (Lilly, Indianapolis, IN).

The experimental protocol consisted of three procedures: (1) blood collection before and after forearm venous occlusion, (2) incubation of the separated plasma to allow the plasminogen-activator present to activate plasminogen to plasmin and to allow the subsequent generation of $\alpha_2$-plasmin inhibitor-plasmin complexes and (3) assay by ELISA for $\alpha_2$-plasmin inhibitor-plasmin complexes and conversion of the results using standard curves to determine plasminogen activator activity.

Blood Collection

Venous blood was drawn into plastic syringes from volunteers less than 1 min after the application of a standard, adult venipuncture tourniquet and added to 3.8% sodium citrate (9:1, vol/vol) in plastic tubes. Blood was then collected from the opposite arm following venous occlusion of the forearm by a sphygmomanometer cuff inflated to 20 mm Hg below systolic pressure for 10 min; [Kwaan et al., Clin. Sci., 15: 254 (1956); Sherry et al., J. Clin. Invest., 38: 810-822 (1959)]. Prior to release of pressure, the venous blood sample was obtained. The plasma, harvested following centrifugation at 2,500 rpm for 10 min, was utilized within 30 min of venipuncture in the plasmin inhibitor-plasmin complex generation assay (vide infra) and was also frozen in plastic tubes at $-70°$ C. for subsequent analysis of salicylate and VIII:Rag concentrations and for use in the generation of standard curves.

Plasma Incubation and ELISA

Figure 7:
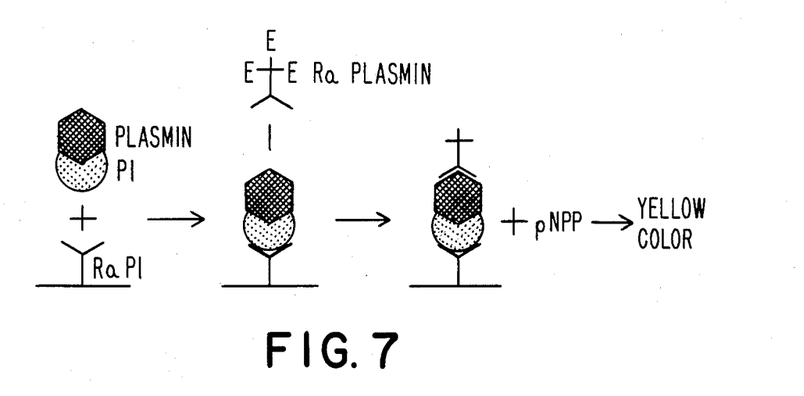
FIG. 7. Enzyme-linked immunosorbent assay (ELISA) for $\alpha_2$-plasmin inhibitor-plasmin complexes.

Assays for plasminogen activator activity were performed in duplicate. Plasma was mixed with an equal volume of Tris (0.1 M)-HCl buffer pH 7.4, containing Na EDTA (0.01 M), with or without the addition of Reptilase (0.1 ml/ml plasma, reconstituted according to the manufacturers instructions, Abbott Laboratories, Chicago, IL). A portion was removed at 0 time and following incubation for 2 h at 37° C. and diluted 1/20 in phosphate-buffered saline containing epsilon amino caproic acid (0.05 M) and Tween 20 (0.05%). These samples were assayed in duplicate for $\alpha_2$-plasmin inhibitor-plasmin complexes by an ELISA as described [Harpel, J. Clin. Invest., 68: 46-55 (1981)] and shown diagramatically in FIG. 7. In brief, $\alpha_2$-plasmin inhibitor in the test sample binds to the IgG fraction of rabbit anti-$\alpha_2$-plasmin inhibitor antiserum that has been applied to microtitration plates (Linbro, Flow Laboratories, McLean, VA). Plasmin in complex with the $\alpha_2$-plasmin inhibitor is then recognized by the F(ab')$_2$ fragment of a rabbit antibody to plasmin coupled to alkaline phosphatase. The addition of p-nitrophenyl phosphate yields a yellow color that is proportional to the amount of plasmin inhibitor-plasmin complex present. Standard curves were prepared either from pooled normal plasma or from the donor's preocclusion plasma. $\alpha_2$-plasmin inhibitor-plasmin complexes were generated by the addition of 0.5-7 units of melanoma TPA/ml plasma prior to clotting with Reptilase and then incubating the sample for 2 H at 37° C. The change in absorbance in the ELISA for $\alpha_2$-plasmin inhibitor-plasmin complexes was plotted against units of TPA added to determine a dose-response standard curve.

Data Analysis

Standard curves were analyzed either by the four parametric logistic method of Rodbard and Hutt [Rodbard et al., Radioimmunoassay and Related Procedures in Medicine, Vienna, International Atomic Energy Agency, I: 165-192 (1974)] or by regression analysis to determine the curve of best fit. The spontaneous activity measured in the subjects' pre- and post-occlusion plasma samples was then converted to units of tissue activator by reference to the standard curve.

In order to rule out any influence of salicylate on the assay, the following standard curve controls were performed. As noted above, blood was drawn from subjects 2 h after the ingestion of 650 mg ASA. It is well documented that the plasma ASA concentration is barely detectible at this time after ingestion (0-1 $\mu$g/ml) while the salicylate concentration (SA) is near its maximum (25-50 $\mu$g/ml); [Rowland et al., J. Pharmaceut. Sci., 56: 717-720 (1967); Rowland et al., J. Pharmaceut. Sci., 61: 379-385 (1972); Mason et al., J. Pharmaceut. Sci., 70: 262-265 (1981)]. ASA (0-1 $\mu$g/ml) or SA (0-70 $\mu$g/ml) were added to the assay at two different times. Additions were made to control, pooled human plasma prior to clotting with Reptilase to determine if ASA or SA interfered with the generation of $\alpha_2$-plasmin inhibitor-plasmin complexes in the in vitro system as described above. TPA (0-7 u/ml) was added, and the changes in absorbance in the presence of various amounts of SA or ASA compared. Additions of SA or ASA were also made after $\alpha_2$-plasmin inhibitor-plasmin complexes had been generated by adding TPA (0-7 u/ml) to plasma which had been clotted with Reptilase. The ELISA was performed and the change in absorbance of samples containing identical amounts of TPA and various amounts of SA or ASA compared to determined whether SA or ASA interfered with the performance of the ELISA. In neither case did the presence of SA or ASA alter the shape of the standard curve ($P>0.4$; 2-way ANOVA) indicating that differences between a subject's TPA response to venous occlusion in the presence or absence of ASA was not due to any influence of SA or ASA on the assay system.

As a second control, standard curves were generated by adding exogenous TPA (0-4 U/ml) to portions of each subject's own preocclusion plasma from each day of the test. Thus, the amount of TPA was determined by comparing changes in absorbance generated by the subject's test plasma in the ELISA to a standard curve generated in a second portion of the same subject's plasma. In this manner control samples were read against standard curves generated in control plasma from the same subject, and aspirin samples were read against standard curves generated in the subject's own aspirin-treated plasma. This controlled for individual variations including salicylate levels and potential effects of these variations on the performance of the ELISA. Results were identical regardless of whether pooled plasma standard curves run on the day of the assay, subject's plasma standard curves as described, or composite standard curves generated by averaging the results of many standard analyses were used to determine TPA concentrations. In this Example, TPA concentrations reported are those determined by using the subject's own plasma for standard curve interpolation.

The amount of TPA present in pre-occlusion and post-occlusion plasma samples was determined by referring to standard curves as described above. Since hemoconcentration occurred during the 10 min of venous occlusion, post-occlusion TPA values were corrected by multiplying the calculated TPA concentration by a correction factor obtained by the formula: 1-post-occlusion hematocrit/1-pre-occlusion hematocrit.

Analysis of VIII:Rag

Factor VIII related antigen (VIII:Rag) in these plasma samples was assayed by quantitative immunoelectrophoresis [Zimmerman et al., *J. Lab. Clin. Med*, 86: 152-159 (1975)] using a monospecific antiserum.

Analysis of Plasma Salicylate

Salicylate concentrations in subjects' plasma were determined by minor modifications of the method of Amick and Mason utilizing toluic acid (Sigma) as an internal standard; [Amick et al., *Anal. Lett.*, 12: 629-640 (1979)]. Extraction of subjects' plasma samples and samples of pooled plasma to which sodium salicylate (0-75 μg/ml; Sigma, St. Louis, MO) had been added were extracted with benzene: ethyl acetate (1:1 v/v, Fisher, Fairlawn, NJ) after rapidly mixing the samples in a vortex mixer for 3 min. This procedure yielded 92-100% recovery of standards. After solvent evaporation to dryness under $N_2$ at 0° C. to prevent SA loss due to sublimation, samples were analyzed by reverse-phase high pressure liquid chromatography utilizing a microprocessor controlled, automated system consisting of Model 720 System Controller, Model 730 Data Module, Model 710B Sample Processor, Models 6000A and 45 solvent delivery systems and a Model 480 Detector, all from Waters Associates (Milford, MA). The mobile phase was $H_2O$: acetonitrile (80:20, v/v, Fisher) containing 1% glacial acetic acid run at a rate of 3 ml per minute on a radial compression Bondapsk $C_{18}$ column (Waters). A standard curve was generated by analyzing plasma samples containing 0-75 μg/ml SA in triplicate. Regression analysis of SA observed vs SA added yielded a straight line of the form $y=0.94x+1$; $r=0.997$. Concentrations of SA in subjects' plasma were determined in duplicate by reference to the standard curve.

Statistical Analysis

The significance of differences noted in single comparisons was determined by the paired or unpaired students t-test (T-test) while the significance of the influence of multiple factors and their interactions was analyzed by one-, two-, or three-way analysis of variance (ANOVA).

Results

Seven men and six women were enrolled in the study. The characteristics of the subjects are listed in Table V.

TABLE V

| SUBJECT CHARACTERISTICS | | | | | |
|---|---|---|---|---|---|
| | N | AGE | HCT | TPA | VIII:Rag |
| MEN | 7 | 35.3 ± 8.0 | 44.1 ± 1.5 | 0.15 ± 0.11 | 116 ± 93 |
| WOMEN | 6 | 32.7 ± 7.0 | 40.7 ± 2.6 | 0.56 ± 0.59 | 128 ± 34 |
| TOTAL | 13 | 34.1 ± 7.3 | 42.5 ± 2.6 | 0.34 ± 0.44 | 122 ± 70 |
| P | | 0.271 | 0.007 | 0.049 | 0.392 |

Figure 8:
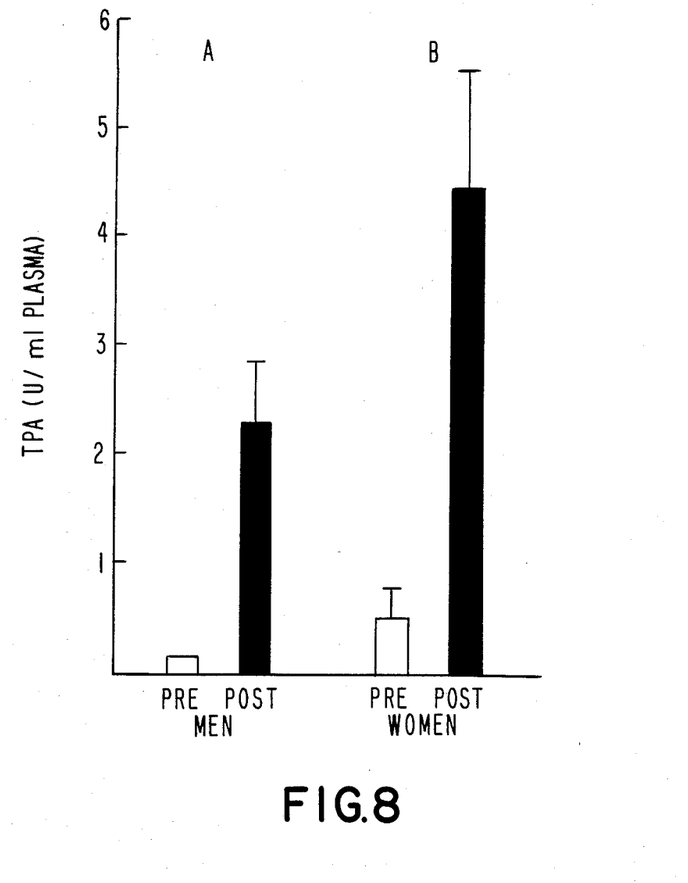
FIG. 8. Effect of venous occlusion on tissue plasminogen activator (TPA) activity.
Figure 9:
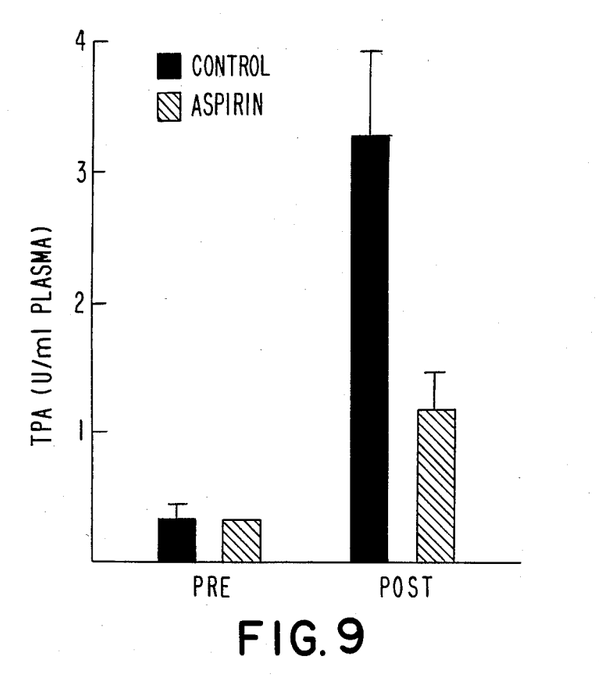
FIG. 9. Effect of aspirin on tissue plasminogen activator (TPA) activity before and after venous occlusion in 13 subjects.

FIGS. 8 and 9 show the mean ±SD. Blood values listed were obtained from the preocclusion venous sample in the control state. Tissue plasminogen activator (TPA) activity is expressed in Units/ml plasma. Factor VIII related antigen (VIII:Rag) concentrations are expressed as percent of the control, pooled plasma=100%. Differences between men and women were analyzed by the unpaired t-test.

While the ages of the men and women were similar (p=0.271), women had lower hematocrits (p=0.007). The "resting level" of TPA defined as the amount of plasminogen activator activity present in venous blood obtained after less than 1 minute of venous occlusion induced by the application of a standard adult, venipuncture tourniquet, was significantly greater in women (0.56 U/ml) than in men (0.15 U/ml, p=0.049). These results are similar to those of previous studies which have found fibrinolytic activity to be greater in premenopausal women than in men; [Cash, *Br. Med. J.*, 2: 502-506 (1966)], and are similar to preocclusion values recently demonstrated using other, sensitive assays; [Comp et al., *J. Lab. Clin. Med.*, 97: 637-645 (1981); Rijken et al., *J. Lab. Clin. Med.*, 101: 274-284 (1983)]. No plasminogen activator activity was measurable in unclotted plasma samples thereby eliminating a contribution of UK-like activity in resting plasma. While both the hematocrit and TPA concentrations were different in men and women, there was no relationship between the hematocrit and the resting level of TPA by linear regression analysis.

The effect of 10 min of forearm venous occlusion induced by a sphygmomanometer cuff inflated to 20 mm Hg below the systolic pressure on TPA concentrations is shown in FIG. 8. The stimulus of venous occlusion induced a 15-fold rise in TPA concentrations in men (0.15±0.11 to 2.28±1.49, mean ±SD, p=0.004) and an 8-fold rise in women (0.56±0.59 to 4.5±2.66, mean ±SD, p=0.006). While the percentage increase was greater in men, the absolute increase of TPA induced by venous occlusion was greater in women (3.94±2.46) than in men (2.13±1.38). While venous occlusion induced a marked rise in TPA activity, no increase in UK or fibrin independent plasminogen activator activity was detected.

To determine whether ASA affects the increase of TPA activity induced by venous occlusion, the 13 subjects underwent testing on two occasions as described above. As noted, each subject was randomly assigned first to either a control period during which no drugs were taken or an ASA period during which 650 mg of ASA was ingested both 18 h and 2 h prior to testing. The same subject returned a minimum of 10 days later to be tested under the opposite condition.

FIG. 9 demonstrates the effect of ASA on TPA activity before and after venous occlusion in the entire group of 13 men and women. ASA did not affect the preocclusion activity of TPA. The control value was 0.34±0.44 U/ml and the value after ASA ingestion was 0.32±0.12 U/ml (mean ±SD, p=0.34). However, ASA markedly inhibited the rise in TPA activity after venous occlusion. In the control state TPA activity increased to 3.31±2.32 U/ml plasma after venous occlusion while after ASA ingestion TPA activity increased only to 1.22±1.01 U/ml plasma (mean ±SD, N=13, p=0.0005). While gender influenced both the resting activity of TPA and the response of TPA activity to venous occlusion as shown above, gender did not influence the inhibition of TPA activity by ASA. ASA inhibited the increase in TPA activity after venous occlusion by 69% in men (2.14±1.43 to 0.67±0.85, mean ±SD, N=7) and by 70% in women (3.94±2.46 to 1.17±0.54, mean ±SD, N=6; effect of sex on inhibition of TPA activity by ASA: p=0.45). While all subjects showed inhibition of TPA release by ASA, there was marked individual variation with percentage inhibition compared to the control state ranging from 15 to 100%.

Figure 10:
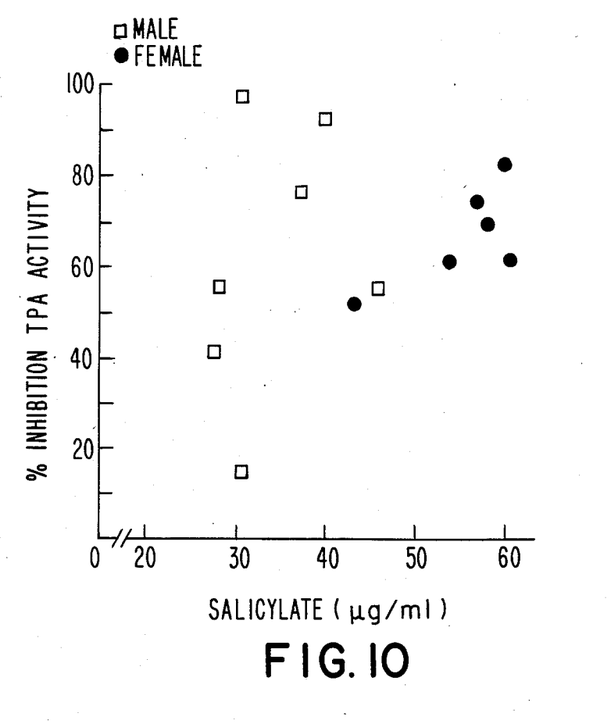
FIG. 10. Relationship between salicylate concentration and inhibition of tissue plasminogen activator (TPA) activity.

To determine whether this marked variability in the suppression of TPA activity by ASA was due to variation in the absorption and metabolism of ASA, salicylate levels were measured in all pre-occlusion plasma samples from both control and ASA test periods. SA levels in all control plasma samples were below the level of detection of the method ($<1$ µg/ml). Plasma SA concentrations after ASA ingestion were significantly higher in women (55.4±6.4 µg/ml, mean ±SD) than in men (34.5±6.8 µg/ml, mean ±SD, p=0.0001). Such findings have been noted previously [Coppe et al., *Thromb. Res.*, 23: 1-21 (1981); Kelton et al., *Thromb. Res.*, 24: 163-168 (1981)]. However, as shown in FIG. 10 there was no significant relationship between percentage inhibition of TPA activity and SA concentration for the group as a whole (r=0.3, p=0.16) or for the women analyzed separately (r=0.7, p=0.06) though a trend did appear to be present in the small group of women. The data indicate that the variability in inhibition of TPA activity was not related to the SA concentrations in the narrow range produced by ingestion of two 650 mg doses. It remains possible that testing of a larger number of subjects taking a range of ASA dosages would demonstrate a significant dose-response relationship, at least for the women.

As noted above, the inhibition of TPA activity was not due to an in vitro effect of either ASA or SA on either the generation of plasmin inhibitor-plasmin complexes or the generation of plasmin inhibitor-plasmin complexes or the performance of the ELISA because addition of ASA (0-1 µg/ml) or SA (0-70 µg/ml) to the assay system at various times did not alter the assay's ability to determine the level of TPA present. Further, the inhibition was not due to an effect of ASA on the resting hematocrit or the extent of hemoconcentration during venous occlusion because there were no differences between the control and ASA period resting hematocrits (42.5±2.6 vs 42.5±2.7) or the increased hematocrits after hemoconcentration due to venous occlusion (50.98±4.4 vs 50.85±3.74, mean ±SD; effect of ASA on hematocrit values: p=0.81, two-way ANOVA).

Figure 11:
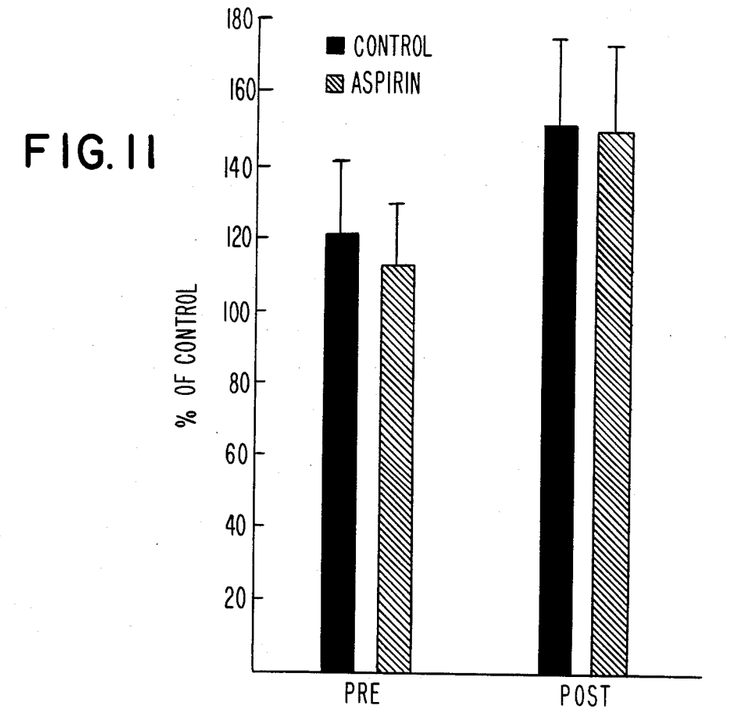
FIG. 11. Effect of aspirin on VIII:Rag concentration pre- and post-occlusion.

Venous occlusion has also been noted to induce a rise in the plasma concentration of VIII:Rag; [Ponari et al., *Thrombosis Res.*, 22: 565-572 (1981)]. The concentrations of VIII:Rag in the same pre- and post-occlusion plasma samples used above were studied to determine whether ASA suppressed this response as well as TPA activity. FIG. 11 shows that venous occlusion induced a significant rise in VIII:Rag concentrations both in the control state (28.5%) and after ASA ingestion (29.4%) but that ASA had no significant effect on VIII:Agn levels (effect of occlusion: p=0.0001; effect of ASA: p=0.795, two-way ANOVA). Thus while ASA caused a marked inhibition of TPA activity after venous occlusion it caused no inhibition of VIII:Rag release.

Figure 12:
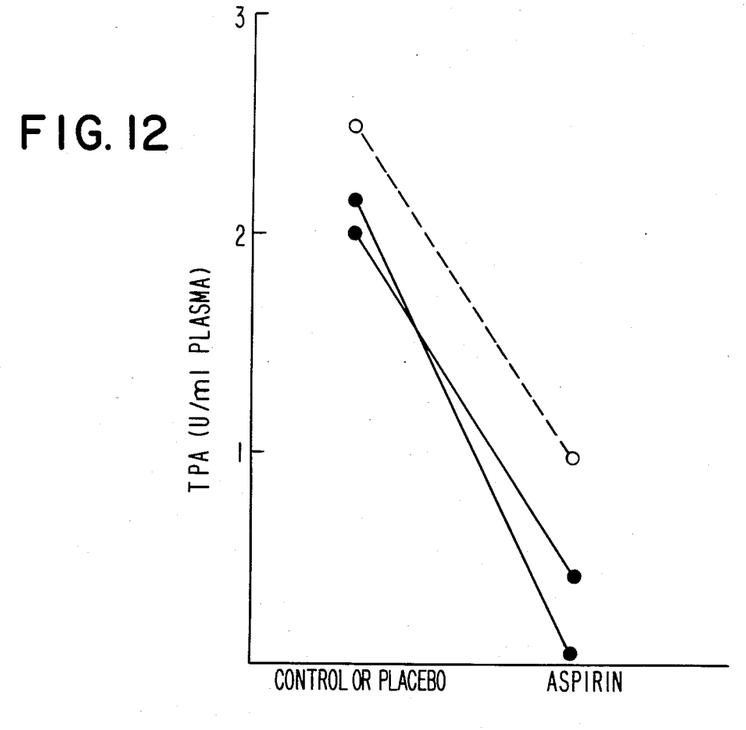
FIG. 12. Consistency of the inhibition of tissue plasminogen activator (TPA) activity by aspirin in a single subject.

To determine whether the inhibition of TPA activity after venous occlusion by ASA was consistent, a single subject was tested on three occasions during a 1 yr period. On two occasions the subject was randomly assigned first to either no drug or ASA and returned 10 days later for the opposite arm of the study. On the third occasion, the subject was randomly assigned first to placebo (lactose) or ASA and the experiment was conducted in a double-blind, placebo-controlled, crossover manner. As shown in FIG. 12, ASA markedly inhibited the rise in TPA from the pre- to post-occlusion state on each of the three test periods including the double-blind cycle. Similar results have been noted in two additional subjects (data not shown). Thus, the inhibition of TPA release by ASA appears to be a consistent response of an individual subject.

Discussion

This study demonstrates that aspirin ingestion produces an inhibition in the vascular plasminogen activator activity induced by venous occlusion. This is due solely to an inhibition of vascular plasminogen activator and not to some other effect of ASA on the test system since it was demonstrated that neither ASA nor SA at concentrations present in vivo in the patient's own plasma inhibited either the generation of $\alpha_2$-plasmin inhibitor-plasmin complexes by exogenous TPA or interfered with the assay method. These observations indicate that ASA inhibits TPA prior to its presence in the circulation, and suggest that ASA is most likely acting by inhibiting release of TPA from the vessel wall. Aspirin did not suppress all phenomena due to venous stasis because neither the increase in VIII:Rag nor the hemoconcentration induced by venous occlusion was affected by ASA. All individuals tested showed inhibition of TPA activity by ASA though there was marked variation in the degree of inhibition ranging from 15% to 100%. This variability, in turn, was not related to SA level. Men and women were affected equally by ASA and this suppressive effect was consistent in the several individuals tested over 9 to 12 months.

Alterations in natural fibrinolysis have been linked to a variety of states. Decreased fibrinolytic activity has been demonstrated in atherosclerosis, vasculitis, and venous thrombosis; [Kernoff et al., *Br. Med. Bull.*, 33: 239-243 (1977); Sarkar, *Nature*, 189: 929-931 (1961); Meade et al., *Adv. Exp. Med. Biol.*, 82: 219-224 (1977)]. Increased fibrinolysis is present in patients with hepatic cirrhosis, in burn victims, during emotional or physical stress, and after venous occlusion, ischemia, electroshock therapy, surgery, intermittent limb compression and the ingestion of onion or garlic; [Sherry et al., *J. Clin. Invest.*, 38: 810-822 (1959); Comp et al., *J. Lab. Clin. Med.*, 97: 637-645 (1981); Sawyer et al., *J. Clin. Invest.*, 39: 426-434 (1960); Allenby et al., *Lancet.*, ii: 1412-1414 (1973); Bordia et al., *Atherosclerosis*, 21: 15-19 (1975); Sharma et al., *J. Postgrad. Med.*, 24: 98-102 (1978); Rem et al., *Br. J. Surg.* 198, 68: 229-233]. Several drugs including epinephrine, pyrogen, nicotinic acid and desamino-d-arginine vasopressin as well as urokinase and streptokinase also induce fibrinolysis; [Collen, *Thromb. Haemostas.*, 43: 77-89 (1980); Sherry et al., *J Clin. Invest.*, 38: 810-822 (1959); Gader et al., *Lancet.*, ii: 1417-1418 (1973)]. It has been suggested repeatedly that the control of natural fibrinolysis may be equal to the coagulation process as contributors to thrombosis. Hence, drugs which alter fibrinolysis may have significant clinical impact. Indeed, there is currently a resurgence in the belief that thrombosis is the inciting event in myocardial infarction and there is great interest in the role of acute thrombolytic therapy with streptokinase or other agents to reestablish coronary blood flow; [Muller, *J. Am. Coll. Cardiol.*, 1: 893-896 (1983)]. Since the role and benefit of ASA therapy in acute and chronic coronary artery disease remain uncertain, the present findings that ASA in "usual" doses inhibits the TPA activity stimulated by venous occlusion adds yet another dimension to the problem.

I claim:

1. A method of determining plasminogen activator induced fibrinolytic activity in human blood which comprises:
   (a) providing plasma samples from freshly drawn blood comprising a first sample which is unclotted and a second sample which has been clotted;
   (b) determining the level of plasmin-naturally occurring plasmin inhibitor complex in both the unclotted and clotted samples first proximate the time of establishment of the samples and again after a time delay sufficient to allow plasminogen activator present in the sample to convert a significant portion of the plasminogen present in the samples to plasmin; and
   (c) comparing the levels of the plasmin-naturally occurring plasmin inhibitor complex in both the unclotted and clotted plasma samples to identify tissue-type plasminogen activator or urokinase-type plasminogen activator contributions to fibrinolytic activity.

2. The method as in claim 1 wherein the clotted and unclotted, plasma samples are provided and the first complex determination made within about thirty minutes from the time that the blood is extracted.

3. The method as in claims 1 or 2 where the fibrinolytic activity is tissue-type plasminogen activator induced and the activity is indicated by a significantly greater increase in complex levels in the clotted sample as compared to the unclotted sample.

4. A method as in claims 1 or 2 where the fibrinolytic activity is urokinase-like plasminogen activator induced and the activity is indicated by a substantially identical level of increase in the clotted sample as compared to the unclotted sample.

5. The method as in claim 1 wherein the level of complex in the samples is determined by a method which comprises:
   (a) forming an insoluble immobilized immunocaptured naturally occurring plasmin inhibitor-plasmin complex comprising plasmin, naturally occurring plasmin inhibitor and plasmin inhibitor antibody or an inhibitor reactive fragment thereof, and
   (b) detecting the plasmin or plasmin inhibitor-plasmin complex in the insoluble immobilized immunocaptured complex.

6. The method of claim 5 wherein immobilized naturally occurring plasmin inhibitor-plasmin complex is affixed to a solid or semisolid matrix by means of the inhibitor antibody or active fragment thereof.

7. The method of claim 5 or 6 wherein:
   (a) the plasma samples are contacted with a complex reactive solid or semisolid matrix have affixed thereon inhibitor antibody or an inhibitor reactive fragment thereof to immunocapture complex from the plasma samples.
   (b) analytically determining the quantity of the captured complex.

8. The method of claim 7 wherein the inhibitor is $\alpha_2$ plasmin inhibitor or $\alpha_2$ macroglobulin.

9. The method of claim 1, 2, 5 or 6 wherein the human blood sample is drawn after venous occlusion sufficient to stimulate tissue-type plasminogen activator activity in said blood.

* * * * *